(12) United States Patent
Laccone

(10) Patent No.: US 8,226,930 B2
(45) Date of Patent: Jul. 24, 2012

(54) SYNTHETIC MECP2 SEQUENCE FOR PROTEIN SUBSTITUTION THERAPY

(76) Inventor: Franco Antonio Laccone, Absdorf (AT)

( * ) Notice: Subject to any disclaimer, the term of this patent is extended or adjusted under 35 U.S.C. 154(b) by 677 days.

(21) Appl. No.: 12/295,856

(22) PCT Filed: Apr. 7, 2006

(86) PCT No.: PCT/EP2006/003203
§ 371 (c)(1),
(2), (4) Date: Jan. 8, 2009

(87) PCT Pub. No.: WO2007/115578
PCT Pub. Date: Oct. 18, 2007

(65) Prior Publication Data
US 2009/0233856 A1   Sep. 17, 2009

(51) Int. Cl.
*A61K 49/00* (2006.01)
*A61K 38/00* (2006.01)
*A61P 25/28* (2006.01)
(52) U.S. Cl. ......... 424/9.1; 514/1.1; 514/17.5; 514/17.7
(58) Field of Classification Search .................. None
See application file for complete search history.

(56) References Cited

U.S. PATENT DOCUMENTS

| | | | |
|---|---|---|---|
| 6,709,817 | B1 | 3/2004 | Zoghbi et al. |
| 2004/0126877 | A1* | 7/2004 | Hur et al. .......... 435/320.1 |

FOREIGN PATENT DOCUMENTS

| | | |
|---|---|---|
| WO | WO-00/62067 | 10/2000 |
| WO | WO-02/085948 | 10/2002 |
| WO | WO-2005/078099 A | 8/2005 |

OTHER PUBLICATIONS

Online Medelian Inheritance in Man, MIM ID 300005, complied 1996-2011, retrieved online Apr. 14, 2011 from <http://www.ncbi.nlm.nih.gov/omim/300005>.*
Masliah, Am J Pathol, 149(3):745-750, Sep. 1996.*
Fichou et al., Neurogenetics, 10:127-133, Epub Nov. 26, 2008.*
Luikenhuis et al., PNAS, 101(16):6033-8. Epub Apr. 6, 2004.*
Lioy et al., Nature, 475(7357):497-500, Jun. 29, 2011.*
Mnatzakanian Gevork N. et al., "A Previously Unidentified MECP2 Open Reading Frame Defines a New Protein Isoform Relevant to Rett syndrom," Nature Genetics, vol. 36, No. 4, Apr. 2004.
Database EMBL [Online] ebi; Mar. 10, 2004, Mnatzakanian et al: "MECP2 isoform B mRNA," retrieved from EBI, Databse accession No. AY541280.
Kosai et al., "58. Rett Syndrome is Reversible and Treatable by MeCP2 Gene Therapy into the Striatum in Mice," Molecular Therapy, Academic Press, vol. 11, Aug. 2005, p. 24.
Jana S. et al., "Strategies for Efficient Production of Heterologous Proteins in *Escherichia coli*," Applied Microbiology and Biotechnology, vol. 67, No. 3, May 2005, pp. 289-298.
Ford K.G. et al "Protein Transduction: An Alternative to Genetic Intervention?" Gene Therapy, vol. 8, No. 1, Jan. 2001, pp. 1-4.
Willard H.F. et al., "Breaking the Silence in Rett Syndrome," Nature Genetics, vol. 23, No. 2, Oct. 1999, pp. 127-128.
Amir Ruthie E. et al., "Rett Syndrome is Caused by Mutations in X-linked MECP2, Encoding Methyl-CpG-binding Protein 2," Nature Genetics, vol. 23, No. 2, Oct. 1999.
Adler, D. A. et al., "The X-linked methylated DNA binding protein, Mecp2, is subject to X inactivation in the mouse", Mammalian Genome, 1995, vol. 6, pp. 491-492.
Amir, Ruthie E. et al., "Rett syndrome is caused by mutations in X-linked MECP2, encoding methyl-CpG-binding protein 2", Nature Genetics, Oct. 1999, vol. 23, pp. 185-188.
Armstrong, Dawna Duncan, "Neuropathology of Rett Syndrome", Mental Retardation and Development Disabilities Reseach Reviews, 2002, vol. 8, pp. 72-76.
Ballestar, Esteban et al., "The impact of MECP2 mutations in the expression patterns of Rett syndrome patients", Hum. Genet., 2005, vol. 116, pp. 91-104.
Chen, Richard Z. et al., "Deficiency of methyl-CpG binding protein-2 in CNS neurons resutls in a Rett-like phenotype in mice", Nature Genetics, Mar. 2001, vol. 27, pp. 327-331.
Counter, Christopher M. et al., "Telomerase activity is restored in human cells by ectopic expression of hTERT (hEST2), the actalytic subunit of telomerase", Oncogene, 1998, vol. 16, pp. 1217-1222.
Derossi, Daniele et al., "The third helix of the antennapedia homeodomain translocates through biological membranes", The Journal of Biological Chemistry, 1994, vol. 269, vol. 14, pp. 10444-10450.
Elliott, Gillian et al., "Intercellular trafficking and protein delivery by a herpesvirus structural protein", Cell, Jan. 24, 1997, vol. 88, pp. 223-233.
Grote, Andreas et al., "JCAT: A novel tool to adapt codon usage of a target gene to its potential expression host", Nucleic Acids Research, 2005, vol. 33, Web Server Issue doi:10.1093/nar/gki376, pp. W526-W531.
Hagberg, Bengt et al., "An update on clinically applicable diagnostic criteria in Retty syndrome", European Journal of Paediatric Neurology, 2002, vol. 6, pp. 293-297.
Ho, Alan et al., "Synthetic protein transduction domains: enhanced transduction potential in vitro and in vivo", Cancer Research, Jan. 15, 2001, vol. 61, pp. 474-477.
Jones, Simon W. et al., "Characteristics of cell-penetrating peptide-mediated peptide delivery", British Journal of Pharmacology, 2005, vol. 145, pp. 1093-1102.

(Continued)

*Primary Examiner* — Daniel E Kolker
*Assistant Examiner* — Stacey MacFarlane
(74) *Attorney, Agent, or Firm* — Birch, Stewart, Kolasch & Birch, LLP

(57) ABSTRACT

The invention relates to the MeCP2 protein and its use in protein substitution therapy. More specifically, the invention relates to condon-optimized nucleic acid sequences for the expression of MeCP2 proteins, methods for creating such a nucleic acid sequence and expressing such a protein, fusions of a protein of the invention to a transduction domain, and vectors and host cells comprising a protein of the invention. Further, the invention relates to uses of nucleic acids or proteins of the invention in medicine, pharmaceutical compositions comprising nucleic acid sequences and proteins of the invention, as well as methods for the treatment, prevention, and/or therapy of neurodegenerative or neurodevelopmental diseases including Rett syndrome.

5 Claims, 8 Drawing Sheets

OTHER PUBLICATIONS

Kane, James F., "Effects of rare condon clusters on high-level expression of heterologous proteins in *Escherichia coli*", Current Opinion in Biotechnology, 1995, vol. 6, pp. 494-500.

Kudo, Shinichi et al., "Functional analyses of MeCP2 mutations associated with Rett syndrome using transient expression systems", Brain & Development, 2001, vol. 23, pp. S165-S173.

Lam, Ching-Wan et al., "Spectrum of mutations in the MECP2 gene in patients with infantile autism and Rett syndrome", J. Med. Genet., 2000, vol. 37, e41.

Lee, Stephen Sung Jae et al., "Spectrum of MECP2 mutations in Rett syndrome", Brain & Development, 2001, vol. 23, pp. S138-S143.

Lithwick, Gila et al., "Hierarchy of sequence-dependent features associated with prokaryotic translation", Genome Res., 2003, vol. 13, pp. 2665-2673.

Lundberg, Ante S. et al., "Immortalization and transformation of primary human airway epithelial cells by gene transfer", Oncogene, 2002, vol. 21, pp. 4577-4586.

Miltenberger-Miltenyi, Gabriel et al., "Mutations and polymorphisms in the human methyl CpG-binding protein MECP2", Human Mutation, 2003, vol. 22, pp. 107-115.

Mnatzakanian, Gevork N. et al., "A previously unidentified MECP2 open reading frame defines a new protein isoform relevant to Rett syndrome", Nature Genetics, Apr. 2004, vol. 36, No. 4, pp. 339-341.

Jones, LaToya S. et al., "Polyanions and the proteome", Molecular & Cellular Proteomics, 2004, vol. 3, No. 8, pp. 746-769.

Nan, Xinsheng et al., "MeCP2 is a transcriptional repressor with abundant binding sites in genomic chromatin", Cell, Feb. 21, 1997, vol. 88, pp. 471-481.

Henaut, A. et al., "Analysis and predictions from *Escherichia coli* sequences, or *E. coli* in silico", Neidhardt FC ed., ASM Press, Washington D.C., vol. 2, Ch. 114, pp. 2047-2066, 1996.

Giacometti, Emanuela et al., : Partial rescue of MeCP2 deficiency by postnatal activation of MeCP2 PNAS, Feb. 6, 2007, vol. 14, No. 6, pp. 1931-1936.

Nagarajan, Raman P. et al., "Reduced MeCP2 expression is frequent in autism frontal cortex and correlates with aberrant MECP2 promoter methylation", Epigenetics, Oct. 2006, vol. 1, No. 4, pp. 172-182.

Becker-Hapak, Michelle et al., "TAT-Mediated Protein Transduction Mammalian Cells", Methods, vol. 24, Issue 3, pp. 247-256, (2001).

Console et al., "Antennapedia and HIV Transactivator of Transcription (TAT) "Protein Transduction Domains" Promote Endocytosis of High Molecular Weight Cargo upon Binding to Cell Surface Glycosaminoglycans", The Journal of Biological Chemistry, vol. 278, No. 37, pp. 35109-35114, (2003).

Dietz, Gunnar P.H. et al., "Delivery of Bioactive Molecules into the Cell: The Trojan Horse Approach", Molecular and Cellular Neuroscience, No. 27, pp. 85-131, (2004).

Falnes et al., "Ability of the Tat Basic Domain and VP22 to Mediate Cell Binding, but Not Membrane Translocation of the Diphtheria Toxin A-Fragment", Biochemistry, vol. 40, No. 14, pp. 4349-4358, (2001).

Fawell et al., "Tat-Mediated Delivery of Heterologous Proteins into Cells", Proc. Natl. Acad. Sci., No. 91, pp. 664-668, (1994).

Fittpaldi et al., "Cell Membrane Lipid Rafts Mediate Caveolar Endocytosis of HIV-1 Tat Fusion Proteins", The Journal of Biological Chemistry, vol. 278, No. 36, pp. 34141-34149, (2003).

Jones, LaToya S. et al., "Polyanions and the Proteome", Molecular & Cellular Proteomics, vol. 3, pp. 746-769, (2004).

Kabouridis, Panagiotis S., "Biological Applications of Protein Transduction Technology", Trends in Biology, vol. 21, No. 11, pp. 498-503, (2003).

Zhao, Ming et al., "Intracellular Cargo Delivery Using Tat Peptides and Derivatives", Medicinal Research Reviews, vol. 24, No. 1, pp. 1-12, (2004).

Ford K.G. et al., "Protein Transduction: An Alternative to Genetic Intervention?" Gene Therapy, vol. 8, No. 1, Jan. 2001, pp. 1-4.

Carney, R. M. et al., "Identification of MeCP2 Mutations in a Series of Females with Autistic Disorder," Pediatric Neurology, 2003, vol. 28, No. 3, pp. 205-211.

Hammer, S. et al., "The Phenotypic Consequences of MECP2 Mutations Extend Beyond Rett Syndrome," Mental Retardation and Developmental Disabilities Research Reviews, 2002, vol. 8, pp. 94-98.

Kuhn, Donald E. et al., "Chromosome 21-derived MicroRNAs Provide an Etiological Basis for Aberrant Protein Expression in Human Down Syndrome Brains," The Journal of Biological Chemistry, 2010, vol. 285, No. 2, pp. 1529-1543.

Smith, Moyra et al., "Mental Retardation, X-Linked, Syndromic 13; MRXS13," Online Mendelian Inheritance in Man (OMIM), Entry No. 300055, pp. 1-6, (2007).

Rasmussen, Sonya A. et al., "Lubs X-Linked Mental Retardation Syndrome; MRXSL," Online Mendelian Inheritance in Man (OMIM), Entry No. 300260, pp. 1-7, (2011).

Kniffen, Cassandra L. et al., "Encephalopathy, Neonatal Sever, Due to MECP2 Mutations," Online Mendelian Inheritance in Man (OMIM), Entry No. 300673, pp. 1-5, (2008).

Ramocki, Melissa B. et al., "Autism and other Neuropsychiatric Symptoms are Prevalent in Individuals with MECP2 Duplication Syndrome," National Institute of Health Public Access, Author Manuscript, Ann Neurol., 2010, pp. 1-20.

Shibayama, A. et al., "MECP2 Structural and 3'-UTR Variants in Schizophrenia, Autism and Other Psychiatric Diseases: A Possible Association With Autism," American Journal of Medical Genetics Part B (Neuropsychiatric Genetics), 2004, 128B, pp. 50-53.

Watson, Pamela et al., "Angelman Syndrome Phenotype Associated with Mutations in MECP2, a Gene Encoding a Methyl CpG, Binding Protein," Journal of Medical Genetics, 2001, vol. 38, pp. 224-228.

Ray, Jasodhara et al., "Proliferation, differentiation, and long-term culture of primary hippocampal neurons", Proc. Natl. Acad. Sci., Apr. 1993, vol. 90, pp. 3602-3606.

Rett, Von A., Wien Med Wochenschr, vol. 116, pp. 723-726, Abstract. (1966).

Schwarze, Steven R. et al., "In vivo protein transduction: delivery of a biologically active protein into the mouse", Science, Sep. 3, 1999, vol. 285, pp. 1569-1572.

Terpe, K., "Overview of tag protein fusions: from molecular and biochemical fundamentals to commercial systems", Appl. Microbial Biotechnol, 2003, vol. 60, pp. 523-533.

Weaving, L. S. et al., "Rett syndrom: clinical review and genetic update", Journal of Medical Genetics, 2005, vol. 42, pp. 1-7, doi:10.1136/jmg.2004.027730.

Xiong, Ai-Sheng et al., "A sinple, rapid, high-fidelity and cost-effective PCR-based two-step DNA synthesis method for long gene sequences", Nucleic Acids Research, 2004, vol. 32, No. 12, e98, doi:10.1093/nar/gnh094.

Yu, Feng et al., "methyl-CpG-binding protein 2 represses LINE-1 expression and retrotransposition by not Alu transcription", Nucleic Acids Research, 2001, vol. 29, No. 21, pp. 4493-4501.

Yusufzai, Timur M. et al., "Functional consequences of Rett syndrome mutations on human MeCP2", Nucleic Acids Research, 2000, vol. 28, No. 21, pp. 4172-4179.

Giacometti, Emanuela et al., : "Partial rescue of MeCP2 deficiency by postnatal activation of MeCP2" PNAS, Feb. 6, 2007, vol. 14, No. 6, pp. 1931-1936.

Guy, Jacky et al., "Reversal of neurological defects in a mouse model of Rett syndrome", Sciencexress, Feb. 8, 2007, doi:10.1126/science.1138689.

\* cited by examiner

SEQUENCE LISTING

<160> NUMBER OF SEQ ID NOS: 54

<210> SEQ ID NO 1
<211> LENGTH: 1494
<212> TYPE: DNA
<213> ORGANISM: Artificial Sequence
<220> FEATURE:
<223> OTHER INFORMATION: codon-optimized sequence

<400> SEQUENCE: 1

```
atggctgctg ctgctgctgc tgctccgtcc ggtggtggtg gtggtggtga agaagaacgt      60
ctggaagaaa aatccgaaga ccaggacctg cagggtctga agacaaaacc gctgaaattc     120
aaaaaagtta aaaagacaa aaagaagaa aagaaggta aacacgaacc ggttcagccg        180
tccgctcacc actccgctga accggctgaa gctggtaaag ctgaaacctc cgaaggttcc     240
ggttccgctc cggctgttcc ggaagcttcc gcttccccga aacagcgtcg ttccatcatc     300
cgtgaccgtg gtccgatgta cgacgacccg accctgccgg aaggttggac ccgtaaactg     360
aaacagcgta aatccggtcg ttccgctggt aaatacgacg tttacctgat caacccgcag     420
ggtaaagctt ccgttccaa agttgaactg atcgcttact tcgaaaaagt tggtgacacc      480
```

```
tccctggacc cgaacgactt cgacttcacc gttaccggtc gtggttcccc gtcccgtcgt    540
gaacagaaac cgccgaaaaa accgaaatcc ccgaaagctc cgggtaccgg tcgtggtcgt    600
ggtcgtccga aaggttccgg taccacccgt ccgaaagctg ctacctccga aggtgttcag    660
gttaaacgtg ttctggaaaa atccccgggt aaactgctgg ttaaaatgcc gttccagacc    720
tccccgggtg gtaaagctga aggtggtggt gctaccacct ccacccaggt tatggttatc    780
aaacgtccgg gtcgtaaacg taaagctgaa gctgacccgc aggctatccc gaaaaaacgt    840
ggtcgtaaac cgggttccgt tgttgctgct gctgctgctg aagctaaaaa aaaagctgtt    900
aaagaatcct ccatccgttc cgttcaggaa accgttctgc cgatcaaaaa acgtaaaacc    960
cgtgaaaccg tttccatcga agttaaagaa gttgttaaac cgctgctggt tccaccctg    1020 ggtgaaaaat ccggtaaagg tctgaaaacc tgcaaatccc cgggtcgtaa atccaaagaa    1080
tcctccccga aggtcgttc ctcctccgct tcctccccgc cgaaaaaaga caccaccac     1140 caccaccacc actccgaatc cccgaaagct ccggttccgt tgctgccgcc gctgccgccg    1200
ccgccgccgg aaccggaatc ctccgaagac ccgacctccc cgccggaacc gcaggacctg    1260
tcctcctccg tttgcaaaga agaaaaaatg ccgcgtggtg gttccctgga atccgacggt    1320
tgcccgaaag aaccggctaa aacccagccg gctgttgcta ccgctgctac cgctgctgaa    1380
aaatacaaac accgtggtga agtgaacgt aagacatcg tttcctcctc catgccgcgt     1440
ccgaaccgtg aagaaccggt tgactcccgt accccggtta ccgaacgtgt ttcc          1494
```

<210> SEQ ID NO 2
<211> LENGTH: 1458
<212> TYPE: DNA
<213> ORGANISM: Artificial Sequence
<220> FEATURE:
<223> OTHER INFORMATION: codon-optimized sequence

<400> SEQUENCE: 2

```
atggttgctg gtatgctggg tctgcgtgaa gaaaaatccg aagaccagga cctgcagggt    60
ctgaaagaca aaccgctgaa attcaaaaaa gttaaaaaag acaaaaaaga gaaaaagaa    120 ggtaaacacg aaccggttca gccgtccgct caccactccg ctgaaccggc tgaagctggt    180
aaagctgaaa cctccgaagg ttccggttcc gctccggctg ttccggaagc ttccgcttcc    240
ccgaaacagc gtcgttccat catccgtgac cgtggtccga tgtacgacga cccgaccctg    300
ccggaaggtt ggaccgtaa actgaaacag cgtaaatccg tcgttccgc tggtaaatac    360 gacgtttacc tgatcaaccc gcagggtaaa gctttccgtt ccaaagttga actgatcgct    420
tacttcgaaa aagttggtga cacctccctg acccgaacg acttcgactt caccgttacc    480
ggtcgtggtt cccgtcccg tcgtgaacag aaaccgccga aaaaccgaa atccccgaaa    540 gctccgggta ccgtcgtgg tcgtggtcgt ccgaaaggtt ccgtaccac ccgtccgaaa    600 gctgctacct ccgaaggtgt tcaggttaaa cgtgttctgg aaaatccc gggtaaactg    660 ctggttaaaa tgccgttcca gacctccccg ggtggtaaag ctgaaggtgg tggtgctacc    720
acctccaccc aggttatggt tatcaaacgt ccgggtcgta aacgtaaagc tgaagctgac    780
ccgcaggcta tccgaaaaa acgtggtcgt aaaccgggtt ccgttgttgc tgctgctgct    840
gctgaagcta aaaaaaaagc tgttaaagaa tcctccatcc gttccgttca ggaaaccgtt    900
ctgccgatca aaaacgtaa aaccgtgaa accgtttcca tcgaagttaa agaagttgtt    960
aaaccgctgc tggtttccac cctgggtgaa aatccggta aaggtctgaa aacctgcaaa    1020
tccccgggtc gtaaatccaa agaatcctcc ccgaaggtc gttcctcctc cgcttcctcc    1080
```

| | |
|---|---|
| ccgccgaaaa aagaacacca ccaccaccac caccactccg aatccccgaa agctccggtt | 1140 |
| ccgctgctgc cgccgctgcc gccgccgccg ccggaaccgg aatcctccga agacccgacc | 1200 |
| tccccgccgg aaccgcagga cctgtcctcc tccgtttgca aagaagaaaa aatgccgcgt | 1260 |
| ggtggttccc tggaatccga cggttgcccg aaagaaccgg ctaaaaccca gccggctgtt | 1320 |
| gctaccgctg ctaccgctgc tgaaaaatac aaacaccgtg gtgaaggtga acgtaaagac | 1380 |
| atcgtttcct cctccatgcc gcgtccgaac cgtgaagaac cggttgactc ccgtaccccg | 1440 |
| gttaccgaac gtgtttcc | 1458 |

<210> SEQ ID NO 3
<211> LENGTH: 810
<212> TYPE: DNA
<213> ORGANISM: Artificial Sequence
<220> FEATURE:
<223> OTHER INFORMATION: codon-optimized sequence

<400> SEQUENCE: 3

| | |
|---|---|
| atcacgaatt cctacggtcg taaaaaacgt cgtcagcgta ggcggccgca gggtggtggt | 60 |
| atggttgctg gtatgctggg tctgcgtgaa gaaaaatccg aagaccagga cctgcagggt | 120 |
| ctgaaagaca aaccgctgaa attcaaaaaa gttaaaaaag acaaaaaaga gaaaaagaa | 180 |
| ggtaaacacg aaccggttca gccgtccgct caccactccg ctgaaccggc tgaagctggt | 240 |
| aaagctgaaa cctccgaagg ttccggttcc gctccggctg ttccggaagc ttccgcttcc | 300 |
| ccgaaacagc gtcgttccat catccgtgac cgtggtccga tgtacgacga cccgaccctg | 360 |
| ccggaaggtt ggacccgtaa actgaaacag cgtaaatccg gtcgttccgc tggtaaatac | 420 |
| gacgtttacc tgatcaaccc gcagggtaaa gctttccgtt ccaaagttga actgatcgct | 480 |
| tacttcgaaa agttggtga cacctccctg gacccgaacg acttcgactt caccgttacc | 540 |
| ggtcgtggtt ccccgtcccg tcgtgaacag aaaccgccga aaaaaccgaa atccccgaaa | 600 |
| gctccgggta ccggtcgtgg tcgtggtcgt ccgaaaggtt ccggtaccac ccgtccgaaa | 660 |
| gctgctacct ccgaaggtgt tcaggttaaa cgtgttctgg aaaaatcccc gggtaaactg | 720 |
| ctggttaaaa tgccgttcca gacctccccg ggtggtaaag ctgaaggtgg tggtgctacc | 780 |
| acctccaccc aggttatggt tatcaaacgt | 810 |

<210> SEQ ID NO 4
<211> LENGTH: 785
<212> TYPE: DNA
<213> ORGANISM: Artificial Sequence
<220> FEATURE:
<223> OTHER INFORMATION: codon-optimized sequence

<400> SEQUENCE: 4

| | |
|---|---|
| ccccccctgc taccacctcc acccaggtta tggttatcaa acgtccgggt cgtaaacgta | 60 |
| aagctgaagc tgacccgcag gctatcccga aaaacgtgg tcgtaaaccg ggttccgttg | 120 |
| ttgctgctgc tgctgctgaa gctaaaaaaa agctgttaa agaatcctcc atccgttccg | 180 |
| ttcaggaaac cgttctgccg atcaaaaaac gtaaacccg tgaaccgtt tccatcgaag | 240 |
| ttaaagaagt tgttaaaccg ctgctggttt ccaccctggg tgaaaaatcc ggtaaaggtc | 300 |
| tgaaaacctg caaatccccg gtcgtaaat ccaaagaatc ctccccgaaa ggtcgttcct | 360 |
| cctccgcttc ctccccgccg aaaaaagaac accaccacca ccaccactcc gaatcccc | 420 |
| cgaaagctcc ggtccgctg ctgccgccgc tgccgccgcc gccgccggaa ccggaatcct | 480 |
| ccgaagaccc gacctccccg ccggaaccgc aggacctgtc ctcctccgtt tgcaaagaag | 540 |

```
aaaaaatgcc gcgtggtggt tccctggaat ccgacggttg cccgaaagaa ccggctaaaa    600
cccagccggc tgttgctacc gctgctaccg ctgctgaaaa atacaaacac cgtggtgaag    660
gtgaacgtaa agacatcgtt tcctcctcca tgccgcgtcc gaaccgtgaa gaaccggttg    720
actcccgtac cccggttacc gaacgtgttt ccggtggtct gtacaaatcc ggttggtccc    780
ccccc                                                                785
```

```
<210> SEQ ID NO 5
<211> LENGTH: 114
<212> TYPE: DNA
<213> ORGANISM: Artificial Sequence
<220> FEATURE:
<223> OTHER INFORMATION: cDNA encoding for the TAT and Strep tag-II
      contained in the pTAT-Strep construct

<400> SEQUENCE: 5
atgattacga attcatatgg acgtaagaag cgtcgtcaac gtaggcggcc gcaatctaga    60
ctcgagccca tggccagatc ttccggatgg agccacccgc agttcgaaaa ataa          114

<210> SEQ ID NO 6
<211> LENGTH: 90
<212> TYPE: DNA
<213> ORGANISM: Artificial Sequence
<220> FEATURE:
<223> OTHER INFORMATION: coding sequence contained in the pET
      28-PP4-6His plasmid

<400> SEQUENCE: 6
atggcatatg caggtaccta tgctcgcgcc gctgcccgcc aggctcgcgc cggtaccggt    60
ggtggcctcg agcaccacca ccaccaccac                                     90

<210> SEQ ID NO 7
<211> LENGTH: 60
<212> TYPE: DNA
<213> ORGANISM: Artificial Sequence
<220> FEATURE:
<223> OTHER INFORMATION: primer

<400> SEQUENCE: 7
agctaagaag cgtcgtcaac gtaggcggcc gcaatctaga ctcgagccca tggccagatc    60

<210> SEQ ID NO 8
<211> LENGTH: 60
<212> TYPE: DNA
<213> ORGANISM: Artificial Sequence
<220> FEATURE:
<223> OTHER INFORMATION: primer

<400> SEQUENCE: 8
ttcgaactgc gggtggctcc atccggaaga tctggccatg gctcgagtc tagattgcgg    60

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
aaacccgaat tcatatggac gtaagaagcg tcg                                 33

<210> SEQ ID NO 10
<211> LENGTH: 33
```

```
-continued

<212> TYPE: DNA
<213> ORGANISM: Artificial Sequence
<220> FEATURE:
<223> OTHER INFORMATION: primer

<400> SEQUENCE: 10
aaacccaagc ttttatttttt cgaactgcgg gtg                                33

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
cccgcggccg caaggcggcg gcatggtagc tgggatgtta ggg                     43

<210> SEQ ID NO 12
<211> LENGTH: 43
<212> TYPE: DNA
<213> ORGANISM: Artificial Sequence
<220> FEATURE:
<223> OTHER INFORMATION: primer

<400> SEQUENCE: 12
gggcaccatg gcgccgccgc cgctaactct ctcggttcac ggg                     43

<210> SEQ ID NO 13
<211> LENGTH: 100
<212> TYPE: DNA
<213> ORGANISM: Artificial Sequence
<220> FEATURE:
<223> OTHER INFORMATION: primer

<400> SEQUENCE: 13
gtcgttccat catccgtgac cgtggtccga tgtacgacga cccgaccctg ccggaaggtt   60
ggacccgtaa actgaaacag cgtaaatccg gtcgttccgc                        100

<210> SEQ ID NO 14
<211> LENGTH: 100
<212> TYPE: DNA
<213> ORGANISM: Artificial Sequence
<220> FEATURE:
<223> OTHER INFORMATION: primer

<400> SEQUENCE: 14
cgtaaatccg gtcgttccgc tggtaaatac gacgtttacc tgatcaaccc gcagggtaaa   60
gctttccgtt ccaaagttga actgatcgct tacttcgaaa                        100

<210> SEQ ID NO 15
<211> LENGTH: 100
<212> TYPE: DNA
<213> ORGANISM: Artificial Sequence
<220> FEATURE:
<223> OTHER INFORMATION: primer

<400> SEQUENCE: 15
tgaagctggt aaagctgaaa cctccgaagg ttccggttcc gctccggctg ttccggaagc   60
ttccgcttcc ccgaaacagc gtcgttccat catccgtgac                        100

<210> SEQ ID NO 16
<211> LENGTH: 100
<212> TYPE: DNA
<213> ORGANISM: Artificial Sequence
```

```
<220> FEATURE:
<223> OTHER INFORMATION: primer

<400> SEQUENCE: 16
gttaaaaaag acaaaaaaga agaaaaagaa ggtaaacacg aaccggttca gccgtccgct      60
caccactccg ctgaaccggc tgaagctggt aaagctgaaa                           100

<210> SEQ ID NO 17
<211> LENGTH: 100
<212> TYPE: DNA
<213> ORGANISM: Artificial Sequence
<220> FEATURE:
<223> OTHER INFORMATION: primer

<400> SEQUENCE: 17
tctgcgtgaa gaaaaatccg aagaccagga cctgcagggt ctgaaagaca aaccgctgaa      60
attcaaaaaa gttaaaaaag acaaaaaaga agaaaaagaa                          100

<210> SEQ ID NO 18
<211> LENGTH: 100
<212> TYPE: DNA
<213> ORGANISM: Artificial Sequence
<220> FEATURE:
<223> OTHER INFORMATION: primer

<400> SEQUENCE: 18
atcacgaatt cctacggtcg taaaaaacgt cgtcagcgtc gtcgtccgca gggtggtggt      60
atggttgctg gtatgctggg tctgcgtgaa gaaaaatccg                          100

<210> SEQ ID NO 19
<211> LENGTH: 100
<212> TYPE: DNA
<213> ORGANISM: Artificial Sequence
<220> FEATURE:
<223> OTHER INFORMATION: primer

<400> SEQUENCE: 19
actgatcgct tacttcgaaa aagttggtga ccctccctg gacccgaacg acttcgactt      60
caccgttacc ggtcgtggtt ccccgtcccg tcgtgaacag                          100

<210> SEQ ID NO 20
<211> LENGTH: 100
<212> TYPE: DNA
<213> ORGANISM: Artificial Sequence
<220> FEATURE:
<223> OTHER INFORMATION: primer

<400> SEQUENCE: 20
ccccgtcccg tcgtgaacag aaaccgccga aaaaaccgaa atccccgaaa gctccgggta      60
ccggtcgtgg tcgtggtcgt ccgaaaggtt ccggtaccac                          100

<210> SEQ ID NO 21
<211> LENGTH: 100
<212> TYPE: DNA
<213> ORGANISM: Artificial Sequence
<220> FEATURE:
<223> OTHER INFORMATION: primer

<400> SEQUENCE: 21
ccgaaaggtt ccggtaccac ccgtccgaaa gctgctacct ccgaaggtgt tcaggttaaa      60
cgtgttctgg aaaaatcccc gggtaaactg ctggttaaaa                          100
```

```
<210> SEQ ID NO 22
<211> LENGTH: 100
<212> TYPE: DNA
<213> ORGANISM: Artificial Sequence
<220> FEATURE:
<223> OTHER INFORMATION: primer

<400> SEQUENCE: 22
gggtaaactg ctggttaaaa tgccgttcca gacctccccg ggtggtaaag ctgaaggtgg      60
tggtgctacc acctccaccc aggttatggt tatcaaacgt                          100

<210> SEQ ID NO 23
<211> LENGTH: 123
<212> TYPE: DNA
<213> ORGANISM: Artificial Sequence
<220> FEATURE:
<223> OTHER INFORMATION: primer

<400> SEQUENCE: 23
gaaaaatccg gtaaaggtct gaaaacctgc aaatccccgg gtcgtaaatc caaagaatcc      60
tccccgaaag gtcgttcctc ctccgcttcc tccccgccga aaaagaaaca ccaccaccac    120
cac                                                                  123

<210> SEQ ID NO 24
<211> LENGTH: 123
<212> TYPE: DNA
<213> ORGANISM: Artificial Sequence
<220> FEATURE:
<223> OTHER INFORMATION: primer

<400> SEQUENCE: 24
caggaaaccg ttctgccgat caaaaaacgt aaaacccgtg aaaccgtttc catcgaagtt      60
aaagaagttg ttaaaccgct gctggtttcc accctgggtg aaaaatccgg taaggtctg      120 aaa                                                                  123

<210> SEQ ID NO 25
<211> LENGTH: 122
<212> TYPE: DNA
<213> ORGANISM: Artificial Sequence
<220> FEATURE:
<223> OTHER INFORMATION: primer

<400> SEQUENCE: 25
tcccgaaaaa acgtggtcgt aaaccgggtt ccgttgttgc tgctgctgct gctgaagcta      60
aaaaaaagct gttaaagaat cctccatccg ttccgttcag gaaaccgttc tgccgatcaa    120
aa                                                                   122

<210> SEQ ID NO 26
<211> LENGTH: 96
<212> TYPE: DNA
<213> ORGANISM: Artificial Sequence
<220> FEATURE:
<223> OTHER INFORMATION: primer

<400> SEQUENCE: 26
cacctccacc caggttatgg ttatcaaacg tccgggtcgt aaacgtaaag ctgaagctga      60
cccgcaggct atcccgaaaa aacgtggtcg taaacc                               96

<210> SEQ ID NO 27
<211> LENGTH: 123
<212> TYPE: DNA
<213> ORGANISM: Artificial Sequence
```

```
<220> FEATURE:
<223> OTHER INFORMATION: primer

<400> SEQUENCE: 27
gcggggaggt cgggtcttcg gaggattccg gttccggcgg cggcggcggc agcggcggca    60
gcagcggaac cggagctttc ggggattcgg agtggtggtg gtggtggtgg tgttctttt     120 tcg                                                                   123

<210> SEQ ID NO 28
<211> LENGTH: 123
<212> TYPE: DNA
<213> ORGANISM: Artificial Sequence
<220> FEATURE:
<223> OTHER INFORMATION: primer

<400> SEQUENCE: 28
tttagccggt tctttcgggc aaccgtcgga ttccagggaa ccaccacgcg gcattttttc    60
ttctttgcaa acggaggagg acaggtcctg cggttccggc ggggaggtcg ggtcttcgga    120
gga                                                                   123

<210> SEQ ID NO 29
<211> LENGTH: 123
<212> TYPE: DNA
<213> ORGANISM: Artificial Sequence
<220> FEATURE:
<223> OTHER INFORMATION: primer

<400> SEQUENCE: 29
cgcggcatgg aggaggaaac gatgtcttta cgttcacctt caccacggtg tttgtatttt    60
tcagcagcgg tagcagcggt agcaacagcc ggctgggttt tagccggttc tttcgggcaa    120
ccg                                                                   123

<210> SEQ ID NO 30
<211> LENGTH: 98
<212> TYPE: DNA
<213> ORGANISM: Artificial Sequence
<220> FEATURE:
<223> OTHER INFORMATION: primer

<400> SEQUENCE: 30
ggatttgtac agaccaccgg aaacacgttc ggtaaccggg gtacgggagt caaccggttc    60
ttcacggttc ggacgcggca tggaggagga aacgatgt                             98

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31 ccccctgta caggccgccg ctaactctct cgg                                   33

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
ggctgcccca aggagccagc taaga                                           25
```

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
acgtaagaag cgtcgtcaac gtaggcggcc gcaggg                             36

<210> SEQ ID NO 34
<211> LENGTH: 100
<212> TYPE: DNA
<213> ORGANISM: Artificial Sequence
<220> FEATURE:
<223> OTHER INFORMATION: primer

<400> SEQUENCE: 34
caacgtaggc ggccgcaggg tggtggtgct gctgctgctg ctgctgctcc gtccggtggt    60
ggtggtggtg gtgaagaaga acgtctggaa gaaaaatccg                        100

<210> SEQ ID NO 35
<211> LENGTH: 65
<212> TYPE: DNA
<213> ORGANISM: Artificial Sequence
<220> FEATURE:
<223> OTHER INFORMATION: primer

<400> SEQUENCE: 35
ttcagcggtt tgtctttcag accctgcagg tcctggtctt cggattttt ttccagacgt     60 tcttc                                                              65

<210> SEQ ID NO 36
<211> LENGTH: 40
<212> TYPE: DNA
<213> ORGANISM: Artificial Sequence
<220> FEATURE:
<223> OTHER INFORMATION: primer

<400> SEQUENCE: 36 cccccccgcat atggagttgc tggtatgctg ggtctgcgtg                         40

<210> SEQ ID NO 37
<211> LENGTH: 43
<212> TYPE: DNA
<213> ORGANISM: Artificial Sequence
<220> FEATURE:
<223> OTHER INFORMATION: primer

<400> SEQUENCE: 37 ccccccccctt gtacagaccg ctaactctct cggtcacggg cgt                    43

<210> SEQ ID NO 38
<211> LENGTH: 39
<212> TYPE: DNA
<213> ORGANISM: Artificial Sequence
<220> FEATURE:
<223> OTHER INFORMATION: primer

<400> SEQUENCE: 38
cccccctcat gaagtatgga cgtaagaagc gtcgtcaac                          39

<210> SEQ ID NO 39
<211> LENGTH: 44

```
<212> TYPE: DNA
<213> ORGANISM: Artificial Sequence
<220> FEATURE:
<223> OTHER INFORMATION: primer

<400> SEQUENCE: 39 gggggggctcg aggccgcctt tttcgaactg cgggtggctc catc        44

<210> SEQ ID NO 40
<211> LENGTH: 53
<212> TYPE: DNA
<213> ORGANISM: Artificial Sequence
<220> FEATURE:
<223> OTHER INFORMATION: primer

<400> SEQUENCE: 40
catatgcagg tacctatgct cgcgccgctg cccgccaggc tcgcgccggt acc     53

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
gccaccaccg gtaccggcgc gagcctggcg        30

<210> SEQ ID NO 42
<211> LENGTH: 37
<212> TYPE: DNA
<213> ORGANISM: Artificial Sequence
<220> FEATURE:
<223> OTHER INFORMATION: primer

<400> SEQUENCE: 42 cccccccatgg catatgcagg tacctatgca cgcgccg        37

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
tttccctcga ggccaccacc ggtaccggcg c        31

<210> SEQ ID NO 44
<211> LENGTH: 42
<212> TYPE: DNA
<213> ORGANISM: Artificial Sequence
<220> FEATURE:
<223> OTHER INFORMATION: primer

<400> SEQUENCE: 44
ccccccccat atggacacca ccatcaccac catcccacca tg        42

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
ctgcacgggc tcatgcttgc cctct        25
```

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
ctcgagtgag atccggctgc taacaaag                                    28

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
ggactccaac gtcaaagggc gaaaaac                                     27

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
cagaagacca ggacctccag ggcc                                        24

<210> SEQ ID NO 49
<211> LENGTH: 23
<212> TYPE: DNA
<213> ORGANISM: Artificial Sequence
<220> FEATURE:
<223> OTHER INFORMATION: primer

<400> SEQUENCE: 49
ctctcgggct caggtggagg tgg                                         23

<210> SEQ ID NO 50
<211> LENGTH: 1539
<212> TYPE: DNA
<213> ORGANISM: Artificial Sequence
<220> FEATURE:
<223> OTHER INFORMATION: codon-optimized sequence

<400> SEQUENCE: 50
tatggacgta agaagcgtcg tcaacgtagg cggccgcagg gtggtggtgc tgctgctgct        60
gctgctgctc cgtccggtgg tggtggtggt ggtgaagaag aacgtctgga gaaaaatcc        120 gaagaccagg acctgcaggg tctgaaagac aaaccgctga attcaaaaa agttaaaaaa        180 gacaaaaaag aagaaaaaga aggtaaacac gaaccggttc agccgtccgc tcaccactcc        240
gctgaaccgg ctgaagctgg taaagctgaa acctccgaag gttccggttc cgctccggct        300
gttccggaag cttccgcttc cccgaaacag cgtcgttcca tcatccgtga ccgtggtccg        360
atgtacgacg acccgaccct gccggaaggt tggacccgta aactgaaaca gcgtaaatcc        420
ggtcgttccg ctggtaaata cgacgtttac ctgatcaacc cgcagggtaa agctttccgt        480
tccaaagttg aactgatcgc ttacttcgaa aaagttggtg acacctccct ggacccgaac        540
gacttcgact tcaccgttac cggtcgtggt tcccgtccc gtcgtgaaca gaaaccgccg        600
aaaaaaccga aatccccgaa agctccgggt accggtcgtg gtcgtggtcg tccgaaaggt        660

```
tccggtacca cccgtccgaa agctgctacc tccgaaggtg ttcaggttaa acgtgttctg      720
gaaaatcccc cgggtaaact gctggttaaa atgccgttcc agacctcccc gggtggtaaa      780
gctgaaggtg gtggtgctac cacctccacc caggttatgg ttatcaaacg tccgggtcgt      840
aaacgtaaag ctgaagctga cccgcaggct atcccgaaaa acgtggtcg taaaccgggt       900 tccgttgttg ctgctgctgc tgctgaagct aaaaaaaaag ctgttaaaga atcctccatc      960
cgttccgttc aggaaaccgt tctgccgatc aaaaaacgta aaacccgtga aaccgtttcc     1020
atcgaagtta aagaagttgt taaaccgctg ctggtttcca ccctgggtga aaatccggt      1080 aaaggtctga aacctgcaa atccccgggt cgtaaatcca agaatcctc cccgaaaggt      1140 cgttcctcct ccgcatcctc cccgccgaaa aagaacacc accaccacca ccaccactcc     1200
gaatccccga agctccggt tccgctgctg ccgccgctgc cgccgccgcc gccggaaccg     1260
gaatcctccg aagacccgac ctccccgccg aaccgcagg acctgtcctc ctccgtttgc     1320
aaagaagaaa aaatgccgcg tggtggtcc ctggaatccg acggttgccc gaagaaccg      1380 gctaaaaccc agccggctgt tgctaccgct gctaccgctg ctgaaaaata caaacaccgt    1440
ggtgaaggtg aacgtaaaga catcgtttcc tcctccatgc cgcgtccgaa ccgtgaagaa    1500
ccggttgact cccgtacccc ggttaccgaa cgtgtttcc                           1539

<210> SEQ ID NO 51
<211> LENGTH: 1506
<212> TYPE: DNA
<213> ORGANISM: Artificial Sequence
<220> FEATURE:
<223> OTHER INFORMATION: codon-optimized sequence

<400> SEQUENCE: 51
tatggacgta agaagcgtcg tcaacgtagg cggccgcagg gtggtggtat ggttgctggt      60
atgctgggtc tgcgtgaaga aaaatccgaa gaccaggacc tgcagggtct gaaagacaaa     120
ccgctgaaat tcaaaaaagt taaaaaagac aaaaagaag aaaagaagg taaacacgaa       180 ccggttcagc cgtccgctca ccactccgct gaaccggctg aagctggtaa agctgaaacc     240
tccgaaggtt ccggttccgc tccggctgtt ccggaagctt ccgcttcccc gaaacagcgt     300
cgttccatca tccgtgaccg tggtccgatg tacgacgacc cgaccctgcc ggaaggttgg     360
acccgtaaac tgaaacagcg taaatccggt cgttccgctg gtaaatacga cgtttacctg     420
atcaacccgc agggtaaagc tttccgttcc aaagttgaac tgatcgctta cttcgaaaaa    480
gttggtgaca cctccctgga cccgaacgac ttcgacttca ccgttaccgg tcgtggttcc    540
ccgtcccgtc gtgaacagaa accgccgaaa aaaccgaaat ccccgaaagc tccgggtacc    600
ggtcgtggtc gtggtcgtcc gaaaggttcc ggtaccaccc gtccgaaagc tgctacctcc    660
gaaggtgttc aggttaaacg tgttctggaa aaatccccgg gtaaactgct ggttaaaatg    720
ccgttccaga cctccccggg tggtaaagct gaaggtggtg gtgctaccac ctccacccag    780
gttatggtta tcaaacgtcc gggtcgtaaa cgtaaagctg aagctgaccc gcaggctatc    840
ccgaaaaaac gtggtcgtaa accgggttcc gttgttgctg ctgctgctgc tgaagctaaa    900 aaaaagctg ttaaagaatc ctccatccgt tccgttcagg aaaccgttct gccgatcaaa     960 aaacgtaaa cccgtgaaac cgtttccatc gaagttaaag aagttgttaa accgctgctg     1020
gtttccaccc tgggtgaaaa atccggtaaa ggtctgaaac ctgcaaatc cccgggtcgt     1080 aaatccaaag aatcctcccc cgaaggtcgt tcctcctccg catcctcccc cgccgaaaaa    1140
gaacaccacc accaccacca ccactccgaa tccccgaaag ctccggttcc gctgctgccg    1200
```

```
ccgctgccgc cgccgccgcc ggaaccggaa tcctccgaag acccgacctc cccgccggaa    1260
ccgcaggacc tgtcctcctc cgtttgcaaa gaagaaaaaa tgccgcgtgg tggttccctg    1320
gaatccgacg gttgcccgaa agaaccggct aaaacccagc cggctgttgc taccgctgct    1380
accgctgctg aaaaatacaa acaccgtggt gaaggtgaac gtaaagacat cgtttcctcc    1440
tccatgccgc gtccgaaccg tgaagaaccg gttgactccc gtaccccggt taccgaacgt    1500
gtttcc                                                               1506
```

<210> SEQ ID NO 52
<211> LENGTH: 513
<212> TYPE: PRT
<213> ORGANISM: Artificial Sequence
<220> FEATURE:
<223> OTHER INFORMATION: fusion protein

<400> SEQUENCE: 52

```
Tyr Gly Arg Lys Lys Arg Arg Gln Arg Arg Pro Gln Gly Gly Gly
  1               5                  10                  15

Ala Ala Ala Ala Ala Ala Pro Ser Gly Gly Gly Gly Gly Gly Glu
                 20                  25                  30

Glu Glu Arg Leu Glu Glu Lys Ser Glu Asp Gln Asp Leu Gln Gly Leu
             35                  40                  45

Lys Asp Lys Pro Leu Lys Phe Lys Lys Val Lys Lys Asp Lys Lys Glu
 50                  55                  60

Glu Lys Glu Gly Lys His Glu Pro Val Gln Pro Ser Ala His His Ser
 65                  70                  75                  80

Ala Glu Pro Ala Glu Ala Gly Lys Ala Glu Thr Ser Glu Gly Ser Gly
                 85                  90                  95

Ser Ala Pro Ala Val Pro Glu Ala Ser Ala Ser Pro Lys Gln Arg Arg
                100                 105                 110

Ser Ile Ile Arg Asp Arg Gly Pro Met Tyr Asp Asp Pro Thr Leu Pro
            115                 120                 125

Glu Gly Trp Thr Arg Lys Leu Lys Gln Arg Lys Ser Gly Arg Ser Ala
130                 135                 140

Gly Lys Tyr Asp Val Tyr Leu Ile Asn Pro Gln Gly Lys Ala Phe Arg
145                 150                 155                 160

Ser Lys Val Glu Leu Ile Ala Tyr Phe Glu Lys Val Gly Asp Thr Ser
                165                 170                 175

Leu Asp Pro Asn Asp Phe Asp Phe Thr Val Thr Gly Arg Gly Ser Pro
            180                 185                 190

Ser Arg Arg Glu Gln Lys Pro Pro Lys Lys Pro Lys Ser Pro Lys Ala
        195                 200                 205

Pro Gly Thr Gly Arg Gly Arg Gly Arg Pro Lys Gly Ser Gly Thr Thr
    210                 215                 220

Arg Pro Lys Ala Ala Thr Ser Glu Gly Val Gln Val Lys Arg Val Leu
225                 230                 235                 240

Glu Lys Ser Pro Gly Lys Leu Leu Val Lys Met Pro Phe Gln Thr Ser
                245                 250                 255

Pro Gly Gly Lys Ala Glu Gly Gly Ala Thr Thr Ser Thr Gln Val
            260                 265                 270

Met Val Ile Lys Arg Pro Gly Arg Lys Arg Lys Ala Glu Ala Asp Pro
        275                 280                 285

Gln Ala Ile Pro Lys Lys Arg Gly Arg Lys Pro Gly Ser Val Val Ala
    290                 295                 300
```

```
Ala Ala Ala Glu Ala Lys Lys Ala Val Lys Glu Ser Ser Ile
305                 310                 315                 320

Arg Ser Val Gln Glu Thr Val Leu Pro Ile Lys Arg Lys Thr Arg
                325                 330                 335

Glu Thr Val Ser Ile Glu Val Lys Glu Val Val Lys Pro Leu Leu Val
            340                 345                 350

Ser Thr Leu Gly Glu Lys Ser Gly Lys Gly Leu Lys Thr Cys Lys Ser
        355                 360                 365

Pro Gly Arg Lys Ser Lys Glu Ser Ser Pro Lys Gly Arg Ser Ser Ser
    370                 375                 380

Ala Ser Ser Pro Lys Lys Glu His His His His His His Ser
385                 390                 395                 400

Glu Ser Pro Lys Ala Pro Val Pro Leu Leu Pro Pro Leu Pro Pro Pro
                405                 410                 415

Pro Pro Glu Pro Glu Ser Ser Glu Asp Pro Thr Ser Pro Pro Glu Pro
            420                 425                 430

Gln Asp Leu Ser Ser Val Cys Lys Glu Lys Met Pro Arg Gly
                435                 440                 445

Gly Ser Leu Glu Ser Asp Gly Cys Pro Lys Glu Pro Ala Lys Thr Gln
    450                 455                 460

Pro Ala Val Ala Thr Ala Ala Thr Ala Ala Glu Lys Tyr Lys His Arg
465                 470                 475                 480

Gly Glu Gly Glu Arg Lys Asp Ile Val Ser Ser Met Pro Arg Pro
                485                 490                 495

Asn Arg Glu Glu Pro Val Asp Ser Arg Thr Pro Val Thr Glu Arg Val
            500                 505                 510

Ser

<210> SEQ ID NO 53
<211> LENGTH: 502
<212> TYPE: PRT
<213> ORGANISM: Artificial Sequence
<220> FEATURE:
<223> OTHER INFORMATION: fusion protein

<400> SEQUENCE: 53

Tyr Gly Arg Lys Lys Arg Arg Gln Arg Arg Pro Gln Gly Gly Gly
1               5                   10                  15

Met Val Ala Gly Met Leu Gly Leu Arg Glu Glu Lys Ser Glu Asp Gln
                20                  25                  30

Asp Leu Gln Gly Leu Lys Asp Lys Pro Leu Lys Phe Lys Val Lys
            35                  40                  45

Lys Asp Lys Lys Glu Glu Lys Glu Gly Lys His Glu Pro Val Gln Pro
50                  55                  60

Ser Ala His His Ser Ala Glu Pro Ala Glu Ala Gly Lys Ala Glu Thr
65                  70                  75                  80

Ser Glu Gly Ser Gly Ser Ala Pro Ala Val Pro Glu Ala Ser Ala Ser
                85                  90                  95

Pro Lys Gln Arg Arg Ser Ile Ile Arg Asp Arg Gly Pro Met Tyr Asp
            100                 105                 110

Asp Pro Thr Leu Pro Glu Gly Trp Thr Arg Lys Leu Lys Gln Arg Lys
        115                 120                 125

Ser Gly Arg Ser Ala Gly Lys Tyr Asp Val Tyr Leu Ile Asn Pro Gln
    130                 135                 140

Gly Lys Ala Phe Arg Ser Lys Val Glu Leu Ile Ala Tyr Phe Glu Lys
145                 150                 155                 160
```

```
Val Gly Asp Thr Ser Leu Asp Pro Asn Asp Phe Asp Phe Thr Val Thr
            165                 170                 175
Gly Arg Gly Ser Pro Ser Arg Arg Glu Gln Lys Pro Pro Lys Lys Pro
            180                 185                 190
Lys Ser Pro Lys Ala Pro Gly Thr Gly Arg Gly Arg Gly Arg Pro Lys
            195                 200                 205
Gly Ser Gly Thr Thr Arg Pro Lys Ala Ala Thr Ser Glu Gly Val Gln
            210                 215                 220
Val Lys Arg Val Leu Glu Lys Ser Pro Gly Lys Leu Leu Val Lys Met
225                 230                 235                 240
Pro Phe Gln Thr Ser Pro Gly Gly Lys Ala Glu Gly Gly Ala Thr
            245                 250                 255
Thr Ser Thr Gln Val Met Val Ile Lys Arg Pro Gly Arg Lys Arg Lys
            260                 265                 270
Ala Glu Ala Asp Pro Gln Ala Ile Pro Lys Lys Arg Gly Arg Lys Pro
            275                 280                 285
Gly Ser Val Val Ala Ala Ala Ala Glu Ala Lys Lys Lys Ala Val
            290                 295                 300
Lys Glu Ser Ser Ile Arg Ser Val Gln Glu Thr Val Leu Pro Ile Lys
305                 310                 315                 320
Lys Arg Lys Thr Arg Glu Thr Val Ser Ile Glu Val Lys Glu Val Val
            325                 330                 335
Lys Pro Leu Leu Val Ser Thr Leu Gly Glu Lys Ser Gly Lys Gly Leu
            340                 345                 350
Lys Thr Cys Lys Ser Pro Gly Arg Lys Ser Lys Glu Ser Ser Pro Lys
            355                 360                 365
Gly Arg Ser Ser Ser Ala Ser Ser Pro Pro Lys Lys Glu His His His
            370                 375                 380
His His His His Ser Glu Ser Pro Lys Ala Pro Val Pro Leu Leu Pro
385                 390                 395                 400
Pro Leu Pro Pro Pro Pro Glu Pro Glu Ser Ser Glu Asp Pro Thr
            405                 410                 415
Ser Pro Pro Glu Pro Gln Asp Leu Ser Ser Ser Val Cys Lys Glu Glu
            420                 425                 430
Lys Met Pro Arg Gly Gly Ser Leu Glu Ser Asp Gly Cys Pro Lys Glu
            435                 440                 445
Pro Ala Lys Thr Gln Pro Ala Val Ala Thr Ala Ala Thr Ala Ala Glu
            450                 455                 460
Lys Tyr Lys His Arg Gly Glu Gly Glu Arg Lys Asp Ile Val Ser Ser
465                 470                 475                 480
Ser Met Pro Arg Pro Asn Arg Glu Glu Pro Val Asp Ser Arg Thr Pro
            485                 490                 495
Val Thr Glu Arg Val Ser
            500

<210> SEQ ID NO 54
<211> LENGTH: 11
<212> TYPE: PRT
<213> ORGANISM: Artificial Sequence
<220> FEATURE:
<223> OTHER INFORMATION: protein transduction domain

<400> SEQUENCE: 54

Tyr Gly Arg Lys Lys Arg Arg Gln Arg Arg
1               5                   10
```

SYNTHETIC MECP2 SEQUENCE FOR PROTEIN SUBSTITUTION THERAPY

FIELD OF THE INVENTION

The present invention relates to the MeCP2 protein and its use in protein substitution therapy. More specifically, the invention relates to codon-optimized nucleic acid sequences for the expression of MeCP2 proteins, methods for creating such a nucleic acid sequence and expressing such a protein, fusions of a protein of the invention to a transduction domain, and vectors and host cells comprising a protein of the invention. Further, the invention relates to uses of nucleic acids or proteins of the invention in medicine, pharmaceutical compositions comprising nucleic acid sequences and proteins of the invention, as well as methods for the treatment, prevention, and/or therapy of neurodegenerative or neurodevelopmental diseases including Rett syndrome.

BACKGROUND OF THE INVENTION

Rett syndrome (RTT) is a progressive neurodevelopmental disorder. It affects almost exclusively females (Rett, 1966, Wien Med Wochenschr 116:723-6) and it is one of the most common causes of mental retardation in females. RTT is characterized by a dynamically clinical course with four consecutive stages. During Stage I (age 6-18 months), girls cease to acquire new skills; they display decelerating head growth and autistic features such as emotional withdrawal and diminished eye contact. In Stage II (age 1-4 years), affected children lose learned skills such as speech and purposeful hand use. They develop irregular breathing patterns, truncal and gait ataxia/apraxia, and stereotypical hand movements. About half the girls also develop seizures and there is some stabilization of the disease during Stage III (age 4-7 years). Seizures become less frequent during Stage IV (age 5-15 years and older), but motor deterioration continues. Hypoactivity, especially among those who cannot walk, contributes to the frequent development of scoliosis, which can cause the girls to be confined to wheelchairs. Neuropathological features of the Rett patients include a decrease in the cortical thickness as well as a reduction of the cortical neuronal size. A strong reduction of the dendritic arborization has also been described but no further gross morphological features are affected (Armstrong, 2002, Ment Retard Dev Disabil Res Rev 8:72-6). RTT is a X-linked disease with an estimated incidence of 1:10,000 to 1:15,000. Amir et al. (1999) (Nat Genet 23:185-8) have identified mutations in the gene MECP2 as the cause of RTT. The MECP2 gene is subject to X-inactivation. Therefore, heterozygous mutant females are mosaic for MeCP2 deficiency and this is most probably one of the modulating factors influencing the phenotype of the disease. Males meeting the clinical criteria for Rett syndrome have been identified in association with a 47,XXY karyotype and from postzygotic MECP2 mutations resulting in somatic mosaicism. For reference, see L. S. Weaving et al.: *Journal of Medical Genetics* 2005; 42:1-7; and G. Miltenberger-Miltenyi, F. Laccone: *Human Mutation* 2003 Volume 22, Issue 2; 107-115.

The MECP2 gene is located on the long arm of the X chromosome at position Xq28 (Adler 1995, Mamm Genome 6(8):491-2). The gene spans 76 kb and is composed of four exons. The MECP2 gene encodes for a protein called methyl-CpG-binding protein 2 (MeCP2), believed to play a pivotal role in silencing other genes. The MeCP2 protein has two isoforms, MeCP2 e1 and MeCP2 e2, formerly called MeCP2B and MeCP2A, respectively (Mnatzakanian et al. 2004, Nat Genet 36:339-41). The isoform e1 is made up of 498 amino acids and isoform e2 is 486 amino acids long. The isoform e1 has a distinctive 21-amino-acid peptide at N terminus including polyalanine and polyglycine tracts. The mRNA of the MECP2 e1 variant has 10-fold greater expression in the brain than that of the MECP2 e2 and it is the most abundant protein isoform in mouse and human brain. MeCP2 is an abundant mammalian protein that selectively binds 5-methyl cytosine residues in symmetrically positioned dinucleotides. CpG dinucleotides are preferentially located in the promoter regions of genes. They represent one of the elements for gene regulation being target for transcriptional silencing factors after DNA methylation.

No successful treatment is yet known to improve the neurological outcome of individuals with Rett syndrome. According to the mutational spectrum of the MECP2 in human (Lam et al. 2000, J Med Genet 37(12):E41; Lee et al. 2001, Brain Dev 23:S138-43) and results from the RTT mouse, there is a general agreement that RTT syndrome is caused by a loss of function of MeCP2. An efficient strategy aiming to restore the MeCP2 activity should be able to compensate the loss of function of MeCP2 in deficient neuronal cells. For reference, see L. S. Weaving et al.: *Journal of Medical Genetics* 2005; 42:1-7; and G. Miltenberger-Miltenyi, F. Laccone: *Human Mutation* 2003, Volume 22, Issue 2; 107-115.

Schwarze et al. (1999, Science 285:1569-1572) report that it is possible to deliver biologically active macromolecules into living cells using a TAT domain (transcriptional transactivator protein of human immunodeficiency virus-1). They show the production of a recombinant TAT-β-galactosidase protein and its injection intraperitoneally into mice. They found that the fusion protein was distributed to all tissues including the brain and the fusion protein was biologically active.

WO 00/62067 (Dowdy et al.) report the use of protein transduction (PTD) molecules including the TAT protein domains for targeting therapeutic molecules in the nervous system.

The production of proteins in heterologous expression systems (i.e. human protein in *Escherichia coli*) requires a corresponding expression vector and the cDNA sequence of the gene of interest. The 64 codons (nucleotide triplets) of the genetic code encode for 20 amino acids and for three translation stop signals. The genetic code is therefore redundant and this means that some amino acids are encoded by more than one codon. Methionine and tryptophane are the only amino acids encoded by one codon, ATG and TGG, respectively, while arginine, leucine and serine are encoded each by six synonymous codons. Because of the degeneration of the genetic code, many alternative nucleic acid sequences encode the same protein. The frequencies of the codons usage vary between the different organisms. These biases can strongly influence the expression of heterologous proteins (Kane, 1995, Curr Opin Biotechnol 6(5):494-500). Codon usage has been identified as the single most important factor in prokaryotic gene expression (Lithwick, 2003, Genome Res 13 (12): 2665-2673).

One objective of the present inventors is therefore to provide constructs encoding for biologically active MeCP2 proteins which are capable of entering cells of the nervous system and compensate for the loss of function of MeCP2 of affected neuronal cells.

A therapeutic approach by delivering TAT-recombinant proteins to the brain could have the tremendous advantage of a possible rapid translation from the animal model to patients. Further advantages might be its easily controllable dosage application, very high delivery efficiency, no concerns inherent to the potentially insertional mutagenenesis or clinical side effects due to the immunological reaction against viral proteins as in case of a gene therapy approach. The PTD-protein delivery approach and its further development might allow the treatment of neurogenetic and devastating diseases like Rett syndrome.

Since attempts to express MeCP2 protein constructs using the human cDNA sequence in amounts sufficient for therapeutic purposes were so far unsuccessful, another objective of the present invention is to provide a MeCP2 expression construct that allows an increased production of recombinant MeCP2 protein.

SUMMARY OF THE INVENTION

Accordingly, the present invention relates to a nucleic acid molecule comprising a first nucleic acid sequence encoding an MeCP2 protein or biologically active fragment or a derivate of said protein or fragment, as defined in the claims. Furthermore, the invention relates to a polypeptide encoded by a nucleic acid molecule, a vector comprising a nucleic acid molecule, and a host cell comprising a vector as defined in the claims. In addition, the invention provides a method for preparing a nucleic acid sequence as defined in the claims as well as a method for producing a polypeptide as defined in the claims. Further, a pharmaceutical composition comprising the nucleic acid molecule and/or a polypeptide according to the claims is provided. The invention also relates to a method of treatment and the use of the nucleic acid molecules and/or the polypeptides for use in medical treatments, as specified in the claims.

DETAILED DESCRIPTION OF THE INVENTION

The present invention arrives at the long-sought goal of providing means and ways to provide recombinant MeCP2 proteins that can be used in therapy of neurodegenerative and neurodevelopmental diseases. The inventors found that by designing and creating optimized MeCP2 nucleic acid sequences, it is for the first time possible to provide MeCP2 proteins as well as fragments or derivatives of such proteins or fragments that may be used for protein substitution therapy methods in mammals.

In a first aspect, the present invention relates to a nucleic acid molecule comprising a first nucleic acid sequence encoding an MeCP2 protein or biologically active fragment or a derivative of the protein or of the fragment, wherein the nucleic acid sequence is codon-optimized for expression in a heterologous cell.

An "MeCP2 protein", as used herein, may be the human isoform e1 (alias isoform B) having the accession number AAS55455 or human isoform e2 (alias isoform A) having the accession number NP_004983 (NCBI protein sequence database), respectively. A skilled person will understand that other human isoforms of MeCP2 or MeCP2 proteins originating from other vertebrates will also be suitable as MeCP2 proteins of the present invention, if these proteins or fragments thereof show similar biological activity as the known human MeCP2 isoforms. The skilled person can readily obtain the sequences of the above-mentioned isoforms and their corresponding m-RNAs from publicly available databases.

The term "biologically active fragment", as used herein, refers to a polypeptide of at least 10, at least 20, at least 30, at least 40, at least 50, at least 60, at least 70, at least 80, at least 90, at least 100, at least 150 or at least 200 amino acids of a MeCP2 protein. A fragment of a MeCP2 protein contains less amino acids than either one of the full-length MeCP2 proteins that can be found under accession number AAS55455 or accession number NP_004983, respectively. A biologically active fragment still exhibits the biological activity of the naturally occurring protein from which it is derived, although not necessarily to the same degree.

A "derivative" of an MeCP2 protein is a polypeptide which is not encoded as such by the genome of a naturally occurring species. In particular, a derivative is a polypeptide that is not identical to one of those polypeptides having the accession numbers of any of the MeCP2 isoforms mentioned above. A derivative, therefore, contains a modification of the naturally occurring MeCP2 proteins, e.g. by amino acid substitution, deletion and addition, but still exhibits the biological activity of the naturally occurring protein, although not necessarily to the same degree. A derivative includes molecules comprising regions that are homologous to an MeCP2 protein by at least 30%, at least 40%, at least 50%, at least 60%, at least 70%, at least 80%, at least 90%, at least 95% or at least 99% identity over an amino acid sequence of identical size, when the two sequences to be compared are aligned by a computer homology program known in the art such as for example the "BLAST" program that is accessible to the public under http://www.ncbi.nlm.nih.gov/BLAST/. A fragment of a derivative of a MeCP2 protein contains less amino acids than a derivative of a MeCP2 protein as defined above.

A "biologically active" fragment or a "biologically active" derivative of a protein or fragment means that the fragment or derivative has at least 50%, at least 60%, at least 70%, at least 80%, at least 90%, at least 95% or at least 100% of the biological activity of an MeCP2 protein as defined above. Whether a MeCP2 protein or fragment or derivative is biologically active can be determined for example by the following tests:

1) A MeCP2 protein or fragment or derivative is considered to be biologically active if it is able to bind to methylated cytosines, and/or to induce a direct recruiting of HDACs and/or to change the acetylation state of histone H3 and histone H4. A general test includes cultivating fibroblasts of Mecp2$^{y/-}$ mice (available from Jackson Laboratory under B6.129P2(C)-Mecp2$^{tm1.1Bird}$/J) and wild-type mice from hind limb/tail tips, for example established according to the protocol described in 3.1 of the experimental section below. Typically, the media will be changed and then the cells incubated for a week at 37° C. with 10% $CO_2$. To test for biological activity e.g. by monitoring the acetylation state of histone H3 and histone H4, mouse fibroblasts of Mecp2$^{y/-}$ animals are treated with, for example, 300 pmol of a MeCP2 protein or a fragment or a derivative of a MeCP2 protein or fragment fused to a transduction domain such as the TAT domain or other transduction domains as described below, and incubated for e.g. 30 h. Cell lysates can then be immunoblotted with antibody against for example histone H3, acetylated histone H3, or acetylated H4K16, as described below. The difference of the acetylation state between treated and untreated fibroblasts is quantified by densitometric analysis as given e.g. in FIG. 5C, and a skilled person will thus be able to determine a change in the histone acetylation state. Examples 5, 6 and 8.1 in combination with FIG. 3 C-D and FIG. 5 below show a way of performing and evaluating such assays.

2) Another possibility to test for the biological activity of a MeCP2 protein or fragment or a derivative of a MeCP2 protein or fragment is a measurement of the level of acetylation of H3 induced by transduction experiments conducted with the proteins to be tested fused to protein transduction domains as described below. Commonly available cell lines such as HeLa oder NIH 3T3 can be used for this purpose. When putting the cells in contact with the fusion proteins, the histone H3 acetylation level will decrease when compared to a control cell line that has a normal level of histone H3 acetylation. It is possible to use this decrease to quantify the biological activity of the produced protein. The evaluation of this test e.g. by Western blot methods is described in the experimental section below.

3) MeCP2 proteins or fragments or derivatives of such proteins can be determined to be biologically active by their ability to bind to methylated cytosines, e.g. by in vitro transcription assays such as described in Nan, X et al., Cell 88: 471-481 (1997), in Yusufzai T. M. and Wolffe, A. P., Nucl. Acids Res. 28: 4172-4179 (2000) or Yu F. et al., Nucl. Acids Res. 29(21):4493-501 (2001).

The term "codon-optimized" nucleic acid sequence as used herein refers to a nucleic acid sequence containing codons that are designed so as to use the codons preferred by the desired host cell, preferably an *E. coli* host cell. A nucleic acid sequence is converted into a codon-optimized nucleic acid sequence having an identical translated polypeptide sequence, but with alternative codon usage, in particular using the most frequently codons of a given organism, e.g. *Escherichia coli*. Such a process is called "backtranslation". A method for selecting and preparing codon-optimized nucleic acid sequences and performing a backtranslation comprises e.g. employing the data from the Class II gene from Henaut and Danchin: Analysis and Predictions from *Escherichia coli* sequences in: *Escherichia coli* and *Salmonella*, Vol. 2, Ch. 114:2047-2066, 1996, Neidhardt F C ed., ASM press, Washington, D.C. Guidance to backtranslating a given protein sequence is also given by the tools available at http://www.prodoric.de/JCat (Grote A. et al., Nucleic Acids Research, 2005, Vol. 33, Web Server issue doi:10.1093/nar/gki376, W526-W531) or the Vector NTI software (Invitrogen). A method of creating a codon-optimized nucleic acid sequence of a MeCP2 protein includes identifying codons in the naturally occurring sequence of a MECP2 gene that are commonly not associated with high expressing *E. coli* genes and replacing them with codons that are known to be widely used in *E. coli* gene expression. A codon-optimized nucleic acid sequence may show improved expression over the naturally occurring sequence in the desired host cell. Whether a codon optimized sequence will induce an improvement in the protein production over the non-optimized sequence can be examined by a skilled person in view of the present disclosure. An example of how to design and create a codon-optimized nucleic acid sequence of the invention is provided in the experimental section below.

A "heterologous" cell as used herein refers to a cell expressing a gene that is not a naturally occurring gene of the particular cell.

In a preferred embodiment, the MeCP2 protein or biologically active fragment or derivative of the protein or fragment is of human origin. More particularly, the MeCP2 protein or a biologically active fragment or derivative of the protein or fragment may be the human MeCP2 isoform e1 or the human MeCP2 isoform e2, or a biologically active fragment or a derivative of these isoforms or these fragments. It will be clear to a skilled person, that other biologically active isoforms of MeCP2 of human or non-human origin or their biologically active fragments or derivatives of the isoforms or fragments can also be used as MeCP2 proteins of the invention.

In another embodiment, the first nucleic acid sequence as defined in the claims has at least 60%, at least 65%, in particular at least 70%, at least 75%, at least 80%, at least 85%, at least 90%, at least 95%, or at least 99% sequence identity to the DNA sequence of codon-optimized human MeCP2 isoform e1 (SEQ ID NO.1) or codon-optimized human MeCP2 isoform e2 (SEQ ID NO.2). A 100% sequence identity is also included. A nucleic acid molecule has "at least x % identity" with SEQ ID NO.1 or SEQ ID NO.2 if, when the nucleic acid sequence in question is aligned with the best matching sequence of SEQ ID NO.1 or SEQ ID NO.2, the sequence identity between those two aligned sequences is at least x %. Such an alignment can be done by a publicly available computer homology program, e.g. the "BLAST" program provided at the NCBI homepage at http://www.ncbi.nlm.nih.gov/BLAST/. While non-functional MeCP2 polypeptides or fragments or derivatives may be useful e.g. for diagnostic purposes, biologically active functional proteins or fragments or derivatives are desirable for therapeutic purposes. The biological activity of such a polypeptide can be determined by the assays described above.

In a further preferred embodiment, the nucleic acid molecule of the invention is expressed in a prokaryotic cell, particularly in a gram-negative or gram-positive cell, for example *E. coli* cells or *Bacillus* sp. cells. Prokaryotic cells suitable for the expression of nucleic acid molecules, e.g. various gram-negative or gram-positive bacteria, are known in the art. The skilled person will also appreciate that other well-known expression systems can be used to achieve protein expression from the nucleic acid molecules of the invention. Such suitable cells can be non-human cells inside or outside the animal body or a human cell outside the human body. Examples are mammalian cells like HEK cells, HELA cells, CHO cells, and others. Examples of cells of non-mammalian origin or even of non-vertebrate origin are *drosophila* Schneider cells, other insect cells like Sf9 cells, yeast cells, other fungal cells, and others.

In another embodiment, the invention provides a nucleic acid molecule of the invention that further comprises a second nucleic acid sequence encoding a polypeptide comprising a protein transduction domain, wherein the second sequence is in operative linkage with the first nucleic acid sequence. Particularly, the nucleic acid molecule comprising a first and second nucleic acid sequence according to the invention is selected from any one of the sequences of SEQ ID NO.50 or SEQ ID NO.51.

Protein transduction domains are protein regions of highly positive charge density, and are able to cross biological membranes by non-classical routes. These regions are usually less than 30 amino acids in length and acquire their basic character and thus their transduction properties from high arginine and, to a lesser extent, lysine contents; reference is made e.g. to Mol. Cell Proteomics. 2004, 3 (8): 746-69. A transduction domain may be obtained from any protein or portion thereof that can assist in the entry into a cell of another protein fused to the transduction domain. The capability of a transduction domain to transduce a protein into a cell can be determined by any conventional method for monitoring protein uptake by cells, typically by FACS sorting or various microscopy techniques like fluorescence microscopy. Protein transduction domains having the ability to transduce a coupled polypeptide can be derived, for example, from the transcriptional transactivator protein of human immunodeficiency virus-1 (TAT protein, accession number AAQ86751), the antennapedia homeodomain (Derossi et al., J. Biol. Chem., 269: 10444 (1994) and HSVVP22 (Elliot and O'Hare, Cell, 88: 223 (1997)), or other protein transduction domains like polyarginine stretches (8 to 10) (for review, see Jones S. W. et al., Br. J. Pharmacol. (2005) 145(8):1093-1102), or the synthetic peptide PTD4 (described in Ho A. et al., Cancer Res. (2001)

15; 61(2):474-477). In a preferred embodiment, the protein transduction domain is derived from the TAT protein. Even more preferred, the nucleic acid sequence encoding a protein transduction domain encodes an amino acid sequence that has at least 60%, at least 65%, in particular at least 70%, at least 75%, at least 80%, at least 85%, at least 90%, at least 95% or 100% sequence identity to the amino acid sequence of the TAT protein transduction domain (YGRKKRRQRRR, SEQ ID NO.54). An amino acid sequence has "at least x % identity" with SEQ ID NO.54 if, when the amino acid sequence in question is aligned with the best matching sequence of SEQ ID NO.54, the sequence identity between those two aligned sequences is at least x %. Such an alignment can be done by a publicly available computer homology program, e.g. the "blastp" program provided at the NCBI homepage at http://www.ncbi.nlm.nih.gov/BLAST/. The skilled person, however, will appreciate that a longer fragment of the TAT protein can also be used as a protein transduction domain.

The term "in operative linkage", as used herein, means a configuration of the nucleic acid sequences of the invention in which one sequence is placed at a position relative to another sequence so that the nucleic acid sequences, after linkage, are in an orientation so that the translational frame of the encoded polypeptides is not altered (i.e. the nucleic acid molecules are linked to each other "in-frame"). The resulting nucleic acid molecule hence encodes an in-frame fusion protein. To achieve this, the nucleic acid sequences of the invention can be organized in several ways. One nucleic acid sequence can be placed at the N-terminus or at the C-terminus of the other sequence, either linked directly or separated by additional linker nucleic acids that are also in-frame with the nucleic acid sequences of the invention. It is also contemplated that one nucleic acid sequence is inserted into another nucleic acid sequence, provided the reading frame of the encoded polypeptide remains intact. If it is desirable that the sequence into which the insertion is placed still encode a functional polypeptide, the biological activity of the polypeptide in question can be evaluated in accordance with the tests described herein.

A linkage of the nucleic acid sequences of the invention can be achieved e.g. by standard ligation methods of DNA manipulation as described in the exemplifying section herein and e.g. Maniatis, T., Fritsch, E. F. & Sambrook, J. (1982) Molecular Cloning: A Laboratory Manual (Cold Spring Harbor Laboratory, Cold Spring Harbor, N.Y.). Other ligation method such as chemical ligation are also contemplated.

In another embodiment, the invention provides a third nucleic acid sequence in operative linkage to a nucleic acid sequence comprising (i) the first nucleic acid sequence or (ii) the first and the second nucleic acid sequence, wherein the third sequence encodes one or more polypeptide sequences suitable for protein purification. Particularly, polypeptide sequences suitable for protein purification include, but are not limited to, a strep tag and/or a his tag and/or a GST tag and/or a intein tag. Such tags facilitate purification of the protein by affinity chromatography, and are well-known in the art (for reference, see e.g. Terpe K., Appl. Microbiol. Biotechnol. (2003) 60(5):523-533). The third nucleic acid sequence is in operative linkage to a nucleic acid sequence comprising the first nucleic acid sequence or the first and the second nucleic acid sequence, i.e. can be placed at a position either at the N-terminus or the C-terminus of either the first or the second nucleic acid sequence. If (1) denotes the first nucleic acid sequence, (2) denotes the second nucleic acid sequence, and (3) denotes the third nucleic acid sequence, possible ways of positioning the sequences include (1)-(2)-(3), (1)-(3)-(2), (2)-(1)-(3), (2)-(3)-(1), (3)-(1)-(2), or (3)-(2)-(1). The nucleic acid sequences can be ligated to each other either directly or can be separated from each other by additional linker nucleic acids. Ligation with or without a linker is effected so as to bring all three nucleic acid sequences in-frame with respect to each other, and the resulting nucleic acid molecule encodes a fusion protein. It is also contemplated that one nucleic acid sequence is inserted into another nucleic acid sequence, provided the reading frame of the encoded polypeptide remains intact. If it is desirable that the sequence into which the insertion is placed still encode a functional polypeptide, the biological activity of the polypeptide in question can be evaluated in accordance with the tests described herein.

In a further embodiment, the nucleic acid molecule of the invention further comprises a fourth nucleic acid sequence in operative linkage to a nucleic acid sequence comprising (i) the first nucleic acid sequence, or (ii) the first and the second nucleic acid sequence, or (iii) the first and the second and the third nucleic acid sequence, said fourth sequence encoding one or more reporter polypeptides. Suitable reporter polypeptides or reporter molecules allow a visualisation and/or localisation of the fusion polypeptide e.g. by optical methods such as fluorescence microscopy. Examples for suitable reporter polypeptides are fluorescent proteins like GFP, CFP and YFP, or enzymes capable of forming a detectable label in a secondary reaction such as horseradish peroxidase, luciferase, or β-galactosidase. Instead of a reporter polypeptide, the skilled person will also contemplate labelling a fusion protein of the invention with another detectable label such as a fluorescent or luminescent organic molecules (e.g. fluorescein, FITC, or Cy5) or by a radioactive label.

The fourth nucleic acid sequence is in operative linkage to a nucleic acid sequence comprising the first nucleic acid sequence or the first and the second nucleic acid sequence or the first and the second and the third nucleic acid sequence, i.e. can be placed at a position either at the N-terminus or the C-terminus of either the first or the second or the third nucleic acid sequence. If (1) denotes the first nucleic acid sequence, (2) denotes the second nucleic acid sequence, (3) denotes the second nucleic acid sequence, and (4) denotes the third nucleic acid sequence, possible ways of positioning the sequences include (1)-(2)-(3)-(4), (1)-(2)-(4)-(3), (1)-(3)-(2)-(4), (1)-(3)-(4)-(2), (1)-(4)-(2)-(3), (1)-(4)-(3)-(2), (2)-(1)-(3)-(4), (2)-(1)-(4)-(3), (2)-(3)-(1)-(4), (2)-(3)-(4)-(1), (2)-(4)-(1)-(3), (2)-(4)-(3)-(1), (3)-(1)-(2)-(4), (3)-(1)-(4)-(2), (3)-(2)-(1)-(4), (3)-(2)-(4)-(1), (3)-(4)-(1)-(2), (3)-(4)-(2)(1), (4)-(1)-(2)-(3), (4)-(1)-(3)-(2), (4)-(2)-(1)-(3), (4)-(2)-(3)-(1), (4)-(3)-(1)-(2), or (4)-(3)-(2)-(1). The nucleic acid sequences can be ligated to each other either directly or can be separated from each other by additional linker nucleic acids. Ligation with or without a linker is effected so as to bring all four nucleic acid sequences in-frame with respect to each other, and the resulting nucleic acid molecule encodes a fusion protein. It is also contemplated that one nucleic acid sequence is inserted into another nucleic acid sequence, provided the reading frame of the encoded polypeptide remains intact. If it is desirable that the sequence into which the insertion is placed still encode a functional polypeptide, the biological activity of the polypeptide in question can be evaluated in accordance with the tests described herein.

In another aspect, the invention relates to a polypeptide encoded by a nucleic acid of the invention. Methods of obtaining polypeptides from nucleic acid molecules are well-known in the art and are described, e.g. by Maniatis et al (supra).

It is also contemplated to obtain a fusion polypeptide by chemical ligation of two or more fragments of a polypeptide of the invention. Chemical ligation methods provide covalent linkages between polypeptides by chemical crosslinking. Suitable cross-linking agents are for example bifunctional crosslinkers such as sulfo-MBS, sulfo-EMCS, sulfo-GMBS, and other crosslinkers available e.g. from the Pierce Chemical Company (Rockford, Ill., USA).

In another aspect, the invention provides a vector comprising the nucleic acid molecules according to the invention. Such a vector can be a plasmid, a phagemid or a cosmid. For example, a nucleic acid molecule of the invention can be cloned into a prokaryotic or eukaryotic expression vector by methods described in Maniatis et al. (supra). Preferably, such a vector is capable of expressing a polypeptide encoded by a nucleic acid molecule of the invention. Such expression vectors typically comprise at least one promoter and can also comprise a signal for translation initiation and a signal for translation termination, or signals for transcriptional termination and polyadenylation. Suitable expression vectors are e.g. the pET28 a+ vector, the pUC18 vector, or the pTRI-Exneo1.1 vector, as described in the Examples below.

In another aspect, the invention relates to a host cell comprising a vector according to the invention. Such a host cell can be a non-human cell inside or outside the animal body or a human cell inside or outside the human body. Other suitable cells include prokaryotic cells, particularly gram-negative or gram-positive bacterial cells. Particularly preferred are *E. coli* cells or *Bacillus* sp. cells. A vector can be transferred into a host cell by a variety of methods well-known in the art. Methods for transfecting host cells and culturing such transfected host cells as well as the conditions for producing and obtaining the polypeptides of the invention from such transformed host cells are also well-known in the art and described, e.g., in Maniatis et al. (supra).

In another aspect, the present invention relates to a method of preparing the nucleic acid sequences or the nucleic acid molecules of the invention, comprising the step of (a) generating a double-stranded nucleic acid molecule by annealing and extending a first set of suitable oligonucleotide primers, wherein the primers comprise nucleic acid sequences of the invention; and (b) optionally repeating the step of (a) with a second, third, or more, set of suitable oligonucleotide primers.

Suitable oligonucleotide primers according to the invention are designed by dividing a nucleic acid sequence of interest into overlapping oligonucleotides, so that the oligonucleotides comprise nucleic acid sequences of the invention. Typically, the range of overlap comprised by these oligonucleotide primers varies from 3 to 100 nucleotides, particularly from 20 to 30 nucleotides. A second, third, or more, set of suitable oligonucleotide primers can be designed so that each primer of the second, third, or more, sets covers a region of the desired nucleic acid sequence of the invention, and may also comprise a range of overlap with one or more of the preceding primers. Preferably, the range of overlap varies between varies between 3 to 100 nucleotides, particularly between 20 to 30 nucleotides.

To achieve an annealing of an oligonucleotide primer according to the invention to one or more other oligonucleotide primers or portions of nucleic acid sequences of the invention, conditions and procedures have to be followed that are well-known in the art. A skilled person will appreciate that the conditions to choose for the annealing procedure depend on various factors such as primer length, length of the overlapping regions, GC content, etc. After annealing, the nucleotide sequence of the primers may be extended by well-known PCR reaction methods or other methods useful for DNA synthesis. Reference is made, for example, to Xiong A. S., et al. (2004), Nucl. Acids Res. 32(12):e98. A method for preparing a nucleic acid sequence according to the invention is illustrated e.g. in Example 1 below.

In a further aspect, the invention relates to a method of producing a polypeptide comprising an MeCP2 protein or a biologically active fragment of an MeCP2 protein or a derivative of an MeCP2 protein or MeCP2 fragment, comprising (a) transforming a host cell with a nucleic acid molecule according to the invention; (b) cultivating the transformed cell under conditions that permit expression of a nucleic acid molecule of the invention to produce a polypeptide comprising an MeCP2 protein or a biologically active fragment or derivative of an MeCP2 protein or fragment; and (c) optionally recovering the polypeptide.

Methods for transforming a host cell with a nucleic acid molecule are well-known in the art. Host cells can be transfected e.g. by methods such as calcium phosphate transfection, electroporation, lipofectin transfection and so on. Host cells can also be transformed by mechanical methods such as microinjection of DNA or by using vectors such as retroviruses. Reference is made to Maniatis et al. (supra). Preferably, the host cell is a prokaryotic cell, more preferably an *E. coli* cell. Conditions for culturing such transfected host cells as well as the conditions that permit an expression of the nucleic acid molecules of the invention to produce polypeptides according to the invention are known to the skilled person and depend e.g. on the type of host cell and the type of vector used to transform the host cell. Examples for culturing host cells and effecting expression of polypeptides of the invention are given in the exemplifying section below. Methods for recovering a polypeptide from a transformed host cell are described e.g. in Roe, S. (ed.), Protein Purification Applications: A Practical Approach. Oxford University Press (2001), Oxford.

In a preferred embodiment, the steps (b) and (c) of the method do not include subjecting the polypeptide to denaturing conditions. Denaturing of a polypeptide, as used herein, refers to the structural changes caused by chemical or physical effects that can lead to a complete or partial loss of the biological activity of the polypeptide. Denaturing of a polypeptide changes the secondary and tertiary structure or conformation of the polypeptide, but usually retains its primary structure. Denaturing can be effected e.g. by changes in temperature, pH, addition of detergents or salts, ultrasonication, and so on. In contrast to the most common strategy of cultivating and recovering polypeptides under denaturing conditions e.g. for purification purposes, the extraction of polypeptides under native conditions may offer the advantage of retaining the functional activity and reducing the intracellular degradation due to misfolding of the polypeptides. Such natively extracted polypeptides of the invention can have high transduction efficiency.

In a preferred embodiment, the polypeptide is present after step (b) of the method in a concentration of greater than 0.5, 1, 2, 3, 4, 5, 6, 7, 8, 9, 10, 11, 12, 13, 14, 15, 16, 17, 18, 19 or 20 mg/l of the bacterial culture. The protein concentration can be quantified by using the Coomassie (Bradford) Protein Assay Kit (Pierce, Rockford, USA) according to the supplier's protocol. In one example, the protein concentration is measured after elution of the sample solution from an affinity column and after desalting. Typically, protein concentration is determined against a set of protein standards such as an albumin standard. The standards are used for calibrating a photometer such as an Eppendorf BioPhotometer (measurement of absorbance e.g. at 595 nm). In an example, 100 μl protein eluate are mixed with 5 ml of "Coomassie Protein Assay Reagent" (Pierce), equilibrated at room temperature for 10 min and then measured in a spectrophotometer. An integrated algorithm calculates the concentration of the sample.

In another aspect, the invention provides a pharmaceutical composition comprising a nucleic acid molecule according to the invention and/or a polypeptide according to the invention, and a pharmaceutically acceptable carrier. A skilled person will be familiar with suitable pharmaceutically acceptable carrier materials.

In another aspect, the invention provides a method of treating a neurodegenerative or a neurodevelopmental disease, comprising administering a polypeptide or a pharmaceutical composition according to the invention to a mammal. Preferably, the mammal is a human subject. Possible administration routes are intravenously, intraperitoneally, intrathecally, subcutaneously, rectally, sublingually, nasally, orally, or transdermally.

Typically, a neurodegenerative disease is a progressive disorder caused by the deterioration and loss of neuronal cells. A neurodevelopmental disease is a disorder caused by a disturbance of the prenatal and, in some cases, of the postnatal brain development. Particularly, the neurodegenerative and neurodevelopmental disorders are due to a reduction of MeCP2 expression or to an impaired function of MeCP2. An impaired function of MeCP2 can be recognized for example by the functional consequences of mutations of the MECP2 gene as described in Yusufzai T. M. and Wolffe A. P., Nucl. Acids Res. (2000), 28(21): 4172-4179, Kudo S. et al., Brain Dev. (2001) Suppl 1:S165-73, and Ballestar E. et al., Hum. Genet. (2005) 116(1-2): 91-104. Generally, mutations of the MBD (methyl-binding-domain) alter the capability of MeCP2 to bind or to be released from the DNA, and thus render it non-functional. Mutations within the TRD (transcription repression domain) typically modify or abolish the transcription repression function of the protein, and lead to an reduction of MeCP2 expression. In view of the foregoing disclosure, the attending medical practitioner will know whether a patient will benefit from, or is suitable for being subjected to, the methods of treatment and/or therapy described herein.

More particularly, the neurodevelopmental disease is Rett syndrome. Rett syndrome is a postnatally neurodevelopmental disorder characterised by a progressive loss of mental abilities, loss of fine and gross motor skills and communicative abilities. A deceleration of head growth as well as the development of different pattern of stereotypic hand movements are usual features of Rett syndrome. Diagnostic criteria have been defined and are helpful for clinical diagnosis (Hagberg B. et al. Eur. J. Paediatr. Neurol. (2002) 6(5):293-7). Tools for diagnosing Rett syndrome include screening for mutations in the MECP2 gene.

In another embodiment, the pharmaceutical composition is administered at a suitable dosage. A skilled person will know procedures useful to establish a suitable dosis for administration. A suitable dosis will lead to a general improvement of the conditions of a mammal suffering from a neurodegenerative and neurodevelopmental disorder due to a reduction of MeCP2 expression or to an impaired function of MeCP2. Effects of a suitable dosage may include an increase of the attention of patient, a reduction of seizures, improved motor skills, and symptoms generally associated with Rett syndrome. Preferably, the pharmaceutical composition is administered at a dosage of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 49, 50, 51, 52, 53, 54, 55, 56, 57, 58, 59, 60, 61, 62, 63, 64, 65, 66, 67, 68, 69, 70, 71, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg of the polypeptide or nucleic acid sequences of the invention per g bodyweight of the mammal. In another embodiment, the pharmaceutical composition of the invention is administered at least once a day, at least every 2, 3, 4, 5, 6 or 7 days.

In another aspect of the invention, the use of a nucleic acid molecule according to the invention for producing a polypeptide comprising an MeCP2 protein or a biologically active fragment or a derivative of an MeCP2 or MeCP2 fragment is provided. Examples for such uses are provided in the examples below.

In a further aspect, the invention relates to a nucleic acid molecule or a polypeptide as described above for use in medicine and/or veterinary medicine. In a further aspect, the invention relates to a use of the nucleic acid molecule or the polypeptide of the invention for the manufacture of a pharmaceutical composition for the prevention and/or therapy of a neurodegenerative or neurodevelopmental disease, as described above. More specifically, the neurodevelopmental disease is caused by a reduction of MeCP2 expression or by an impaired function of MeCP2, as described above. Particularly, the neurodevelopmental disease is Rett syndrome, as described above. The nucleic acid molecule, polypeptide or pharmaceutical composition is in a form suitable for administration to a mammal. Preferably, the mammal is a human subject. Possible administration routes are intravenously, intraperitoneally, intrathecally, subcutaneously, rectally, sublingually, nasally, orally, or transdermally.

B.-D. Expression and distribution of MeCP2e2-EGFP in vitro. B. Top row: microphotographs of a NIH3T3 cell line stably expressing the TAT-MeCP2e2-EGFP fusion protein. About 40% of the cells are expressing the TAT-MeCP2e2-EGFP protein. The arrows point to a cell (shown at higher magnification in the insets) with typical heterochromatic distribution (DAPI) of the MeCP2e2 protein. Lower row: nearly 100% of the HeLa cells are expressing the MeCP2e2 protein. The localization is typically in the nucleus without any cytosolic protein staining. Insets reveal heterochromatic distribution of MeCP2. C. Western Blot of 100 µg of protein extract from NHI3T3 and HeLa untransfected controls (wt) and corresponding cell lines stably expressing TAT-MeCP2e2-EGFP (st) with antibody against acetylated histone H3, polyclonal anti-MeCP2 and anti-alpha tubulin as a loading control. In both stable cell lines the fusion protein has an apparent molecular weight of 100 kDa. D. The densitometric quantification of the Western Blot signals shows a reduction of histone H3 acetylation of 50 to 60% of the cell lines overexpressing the TAT-MeCP2e2-EGFP fusion protein versus the wild type ones.

Figure 4:
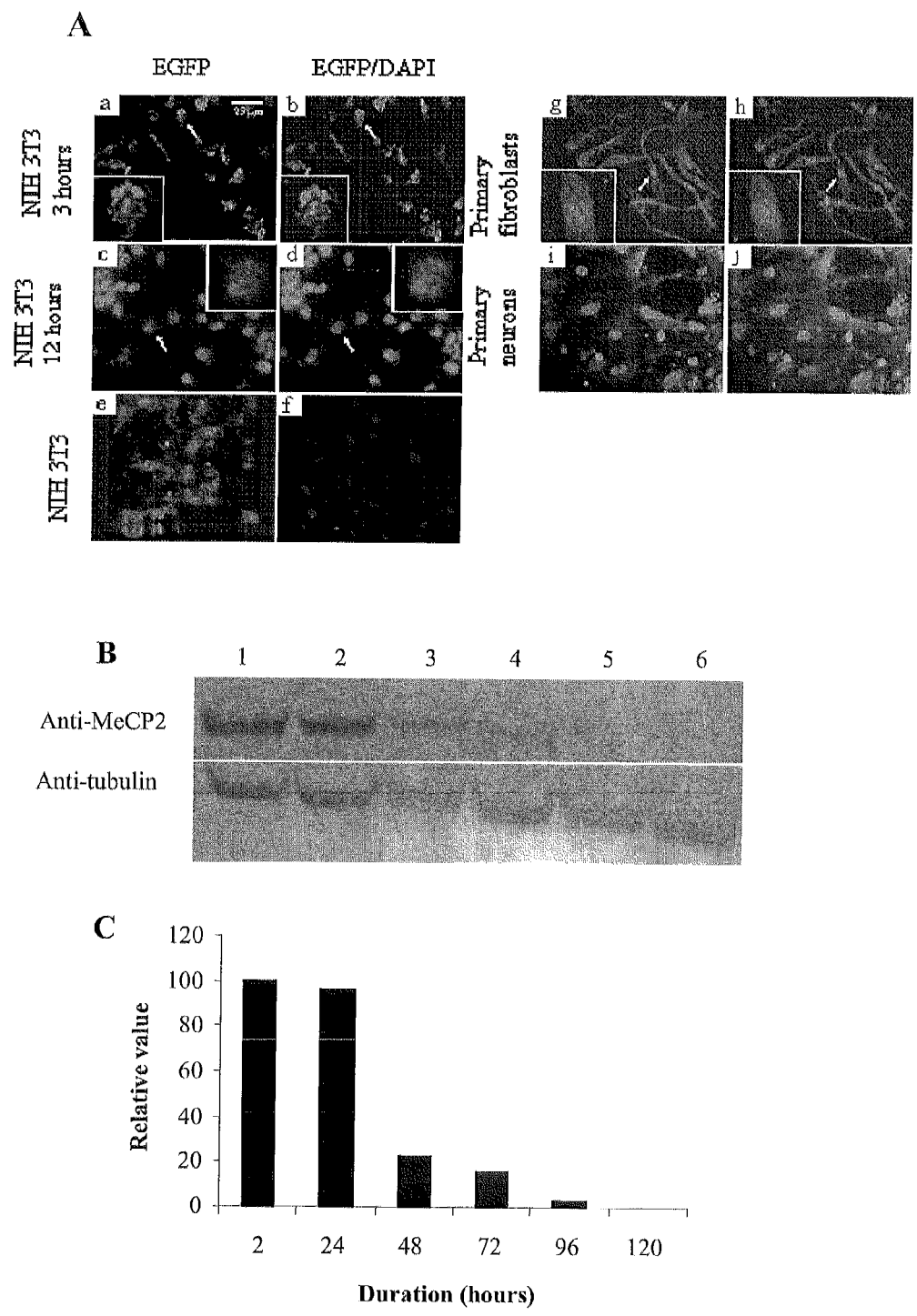

FIG. 4. A. Transduction kinetics and pattern of distribution of TAT-MeCP2e2-EGFP in several cell types. NIH3T3 cells were incubated with 50 µg/ml of TAT-MeCP2e2-EGFP for 3 (a,b) or 12 hours, respectively (c,d). After 3 hours, the cells were only partly transduced and the recombinant protein was located mostly in the cytoplasm visible as gross spots (a,b). After 12 hours of incubation the recombinant protein transduced all the cells and located mostly in the physiological localization, the nucleus. e. Confocal imaging confirms that the protein is mainly located into the nucleus. f. The recombinant EGFP protein without TAT was not able to penetrate the cells at any times and it was just visible as spared extracellular spots (12 hours of incubation). g and h. TAT-MeCP2e2-EGFP was also used to test its transduction efficiency in primary fibroblasts of a Rett patient with the p.T158M. The merged image shows that the protein has efficiently transduced all fibroblasts. The localization is mainly in the nucleus but some protein was still in the cytoplasm (inset). i and j. Primary hippocampal neurons from wild-type mice were incubated with the TAT-MeCP2e2-EFGP fusion protein. The MeCP2e2 protein is easily detectable in the nucleus.

B._C. Time persistence of TAT-MeCP2e2 protein in transduced NIH3T3 cells. NIH3T3 cell cultures have been independently incubated with the same amount of TAT-MeCP2e2 protein. Protein extracts have then been collected from the treated cell cultures at different time points. B. Western blot analysis shows the presence of the recombinant protein at 2, 24, 48, 72, 96 (barely visible) but not at 120 hours post incubation (lane 1 to 6 respectively). C. The densitometric analysis shows the reduction in protein concentration over the time. The maximal drop of about 77% has been observed between 24 and 48 hours. The relative value has been calculated setting the absolute value in lane 1 as 100%. The values at the different time point have then been accordingly changed.

Figure 5:
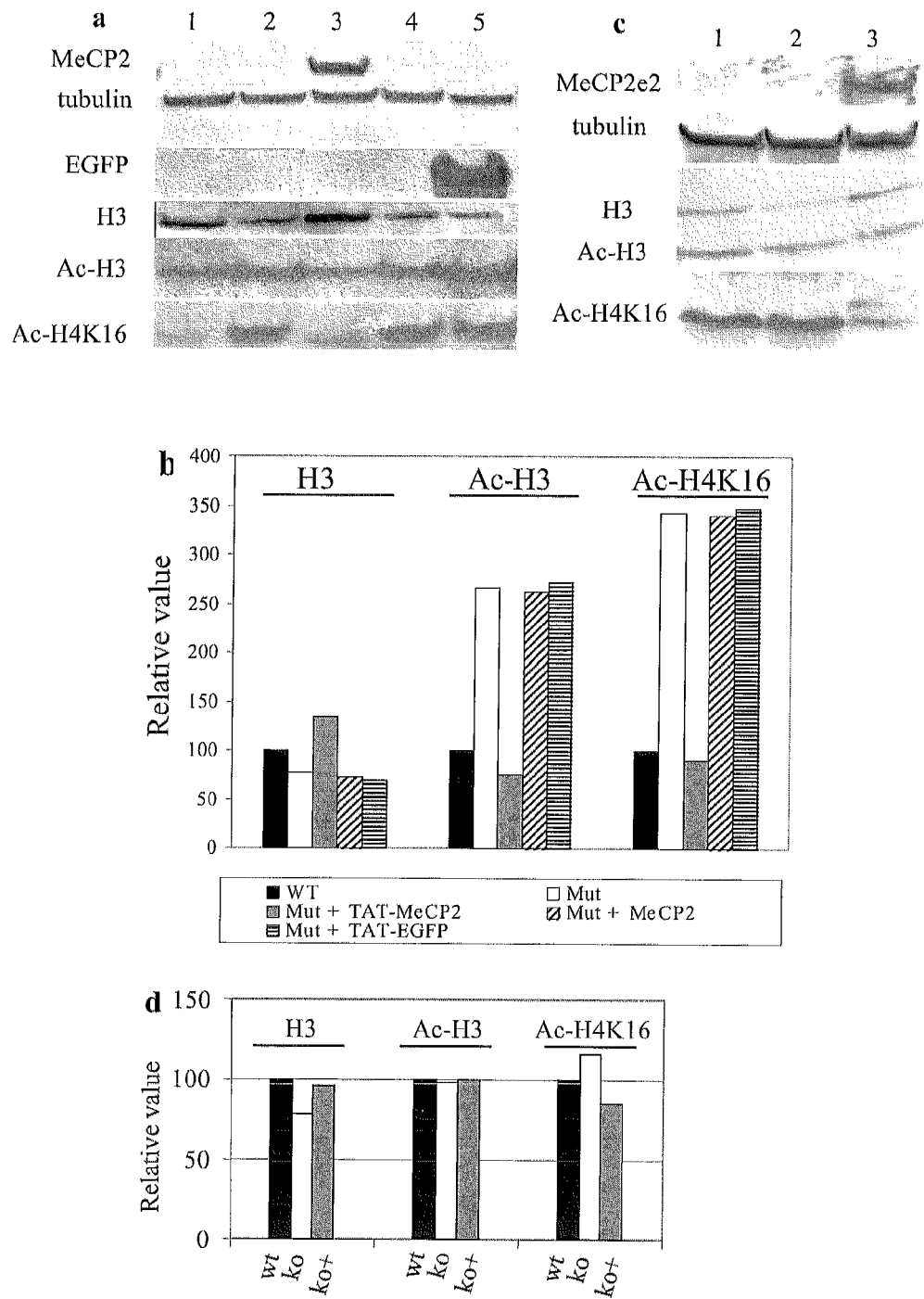

FIG. 5. Mecp2 influences the acetylation of histones H3 and H4K16. a. Protein extracts from monoallelic cell cultures expressing the wt (1) and the mutated MeCP2 (2) (p.T158M mutation) have been analyzed for acetylation state of histone H3 and H4K16. Independent cell cultures of the monoallelic cell line expressing the mutated allele have been incubated respectively with 300 pmol of TAT-MeCP2e2 (3), MeCP2e2 (4) and TAT-EGFP (5) recombinant proteins for 64 hours. The MeCP2 protein was only detectable in the cell line incubated with TAT-MeCP2e2 (3) but not with MeCP2e2. TAT-EGFP successfully transduced the cells and it was detected by the anti-GFP antibody (5). b. The normalized densitometric analysis of the western blot in using tubulin as reference for protein loading revealed a slight reduction of the non-acetylated histone H3 and a hyperacetylation of histones H3 and H4K16 in the monoallelic cell line expressing the mutated allele (Mut) versus the wild type (WT) (white bars versus black ones). The incubation with TAT-MeCP2e2 of the mutated cell line induced a reduction of the hyperacetylation of both H3 and H4K16 and a slight increment of the non acetylated form of H3 (grey bars). No significant changes of the histone acetylation were observed in independent cell cultures by the incubation with a equimolar dosage of MeCP2 without TAT and TAT-EGFP proteins (obliquely and horizontally dashed bars). These results proved that the TAT-MeCP2e2 is biologically active. c. Western blot of fibroblasts extracts of a wt mouse (1), a Mecp2$^{-/y}$ (2) and a MECP2$^{-/y}$ mouse incubated with 300 pmol of TAT-MeCP2e2 (3). The anti-MeCP2 antibody revealed an efficient transduction of the fibroblasts by the recombinant protein. Tubulin was used as reference. d. The normalized densitometric analysis using tubulin as reference protein of the Western blot shown in c. revealed a reduction of the non-acetylated histone H3 form, no increment of the acetylated form of histone H3 but an increment of the acetylated form of the histone H4K16 of Mecp2$^{-/y}$ (ko) versus the wild type mice (wt) (white versus black bars). The incubation of fibroblast cell culture from Mecp2$^{-/y}$ mice with TAT-MeCP2e2 (ko +) induced an increment of the non-acetylated histone H3 (grey bars) and a decrease of the hyperacetylation level of H4K16.

Figure 6:
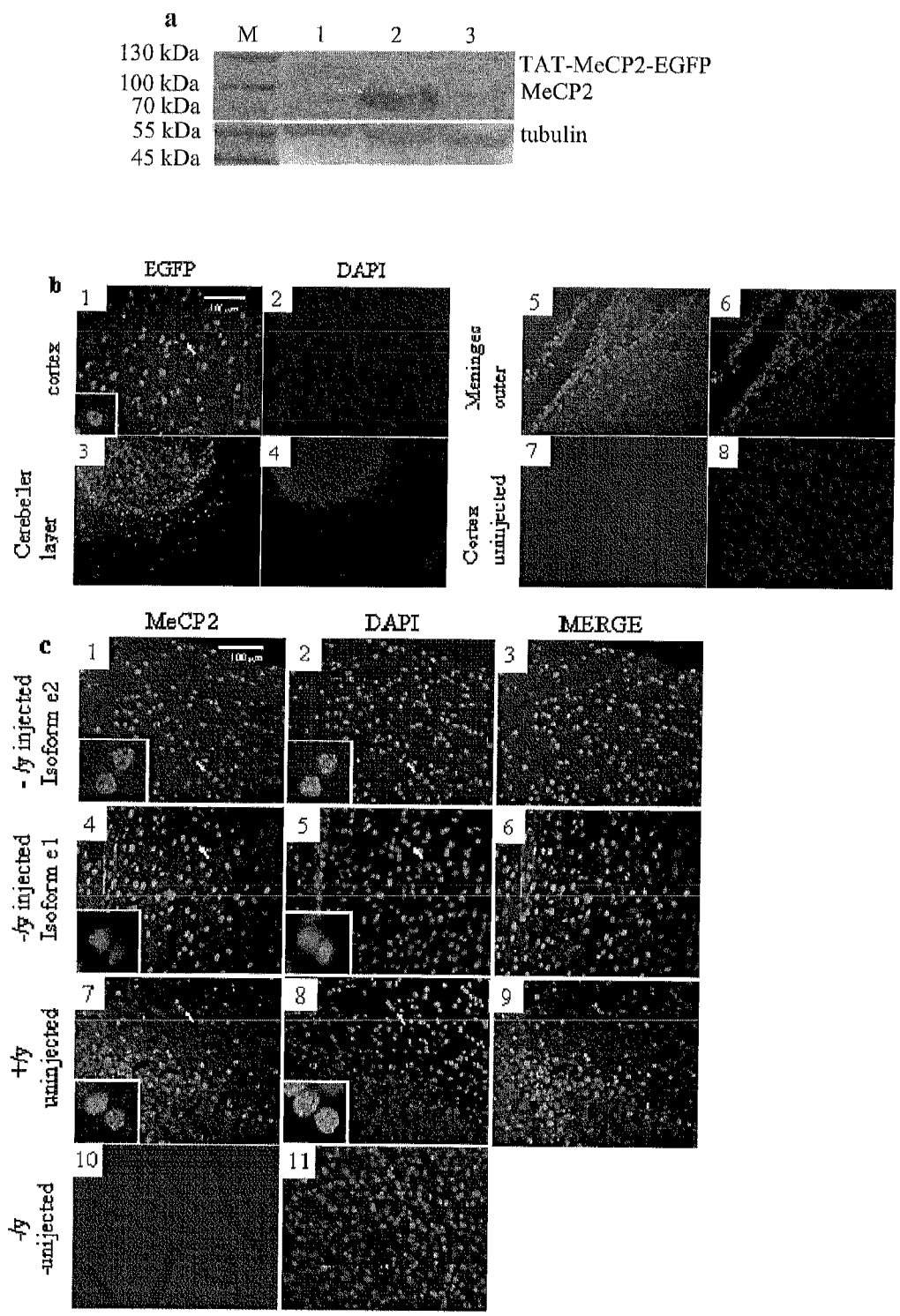

FIG. 6. MeCP2 can be targeted to CNS neurons in vivo. a. Immunoblotting with anti-MeCP2 antibody of 50 µg brain protein lysate of three wt mice sacrificed 20 hours after an independently intraperitoneal injection with TAT-MeCP2e2-EGFP (lane 1), TAT-MeCP2e2 (lane 2) or MeCP2e2 without TAT (lane 3) proteins. In lane 1 the presence of TAT-MeCP2e2-EGFP can be well recognized by the higher molecular weight in respect to the endogenous Mecp2 protein. The mouse injected with TAT-MeCP2e2 revealed much stronger MeCP2e2 protein signal (lane 2) as in lane 1 and 3, where the level of the endogenous Mecp2 is not strongly different. b. GFP immunofluorescence in the brain of wild-type mouse injected with TAT-MeCP2e2-EGFP and EGFP without TAT proteins 20 hours after injection. The GFP signal is localized in nuclei of almost all the cells in cortex, cerebellar granule cell layer and outer meninges in mice injected with TAT-MeCP2e2-EGFP (1 to 6). No EGFP is detectable in the brains of EGFP injected mouse (7 and 8). c. Immunofluorescence of two Mecp2$^{-/y}$ animals injected each with one isoform of recombinant proteins using a polyclonal anti-MeCP2 antibody. The first and second rows depict sections from the cortex of the Mecp2$^{-/y}$ mouse treated for 20 days with recombinant TAT-Mecp2e1 (1,2,3) and e2 (4,5,6). The presence of MeCP2 mainly in the nuclei of the cells is clearly evident in the insets. Brain's slice of one uninjected MeCP2+/y (7,8,9) and one MeCP2$^{-/y}$ mice (10,11) served as controls.

Figure 7:
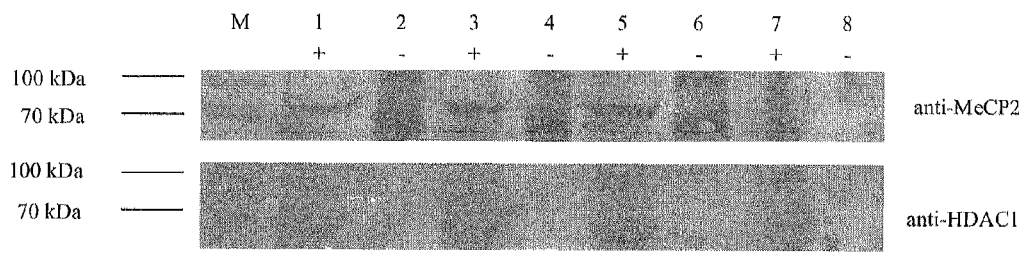
Figure 7:
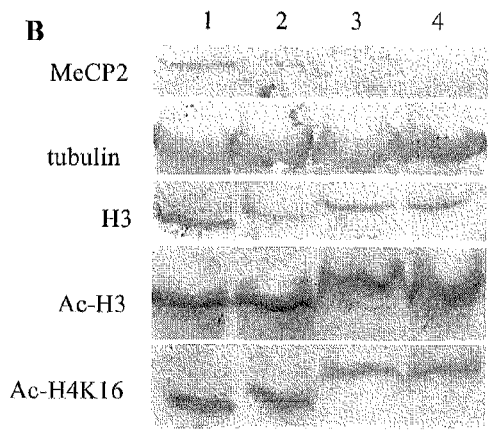
Figure 7:
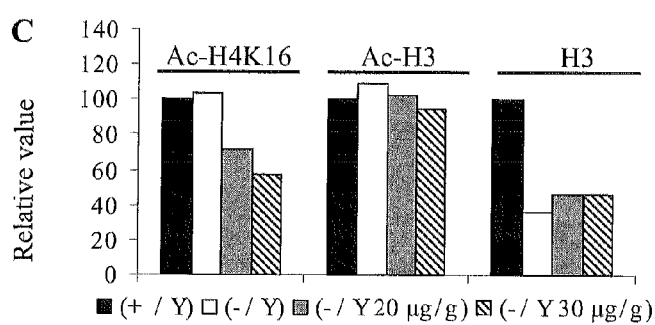

FIG. 7. A. Communoprecipitation experiments in fibroblast cell cultures of Mecp2$^{-/y}$ animals transduced by TAT-MeCP2e1 shows a recruitment of HDAC1. In the top row is a Western blot of the immunoprecipitated protein fractions using an anti MeCP2 polyclonal antibody ("+" precipitated fraction at the presence and "−" at the absence of anti-MeCP2 antibody). In the bottom row is a Western blot analysis from the same immunoprecipitates using an anti-HDAC1 antibody. Lanes 1 and 2: precipitated protein fraction from fibroblasts of a wild type animal. Lanes 3,4 and lanes 5,6: precipitated protein fraction from fibroblasts of Mecp2$^{-/y}$ mice transduced with TAT-MeCP2e1 and TAT MeCP2e2, respectively. Lanes 7 and 8: precipitated protein fraction from fibroblasts of a Mecp2$^{-/y}$ animal. In the immunoprecipitation fractions, the presence of both MeCP2 as well as HDAC1 is visible in the fraction of the positive control (lane 1) as well as in the fractions of cells transduced by both TAT-MeCP2 isoforms (lanes 3 and 5). No detectable Mecp2 as well as HDAC1 protein is visible in the precipitated fraction of negative controls (lane 7). The immunoprecipitates in absence of anti-MeCP2 did not reveal the presence neither of MeCP2 as well as HDAC1.

B._C. TAT-MeCP2 isoforms modulate hyperacetylation of H3 and H4K16 in the brain. B. Mecp2-deficient mice were injected i.p. for 14 days with PBS (lane 2), 20 μg/g (lane 3) or 30 μg/g (lane 4) of TAT-MeCP2e1. 50 μg brain protein extracts from all injected mice (2 to 4) and an uninjected wild-type mouse (1) were immunoblotted with antibodies against histone H3 (H3), acetylated histone H3, acetylated histone H4K16 and MeCP2. The anti alpha-tubulin antibody was used as loading control. Mecp2$^{-/y}$ mice did not show any detectable Mecp2 or recombinant protein (lanes 2, 3 and 4). No evident hyperacetylation of neither H3 nor H4K16 is detectable in PBS injected MeCP2-deficient mice compared to wild-type mice. However, the injection of recombinant protein reduces the acetylation of the histone H4K16. No strong difference were observed for acetylated and non acetylated histone H3. C. Densitometric analysis showing a dose dependent biochemical activity of MeCP2 protein. Analogous experiments have been performed with the TAT-MeCP2e2 protein with consistently similar results. The relative value represents the densitometric values expressed as percentage of the value of the wt animals defined as 100%.

Figure 8:
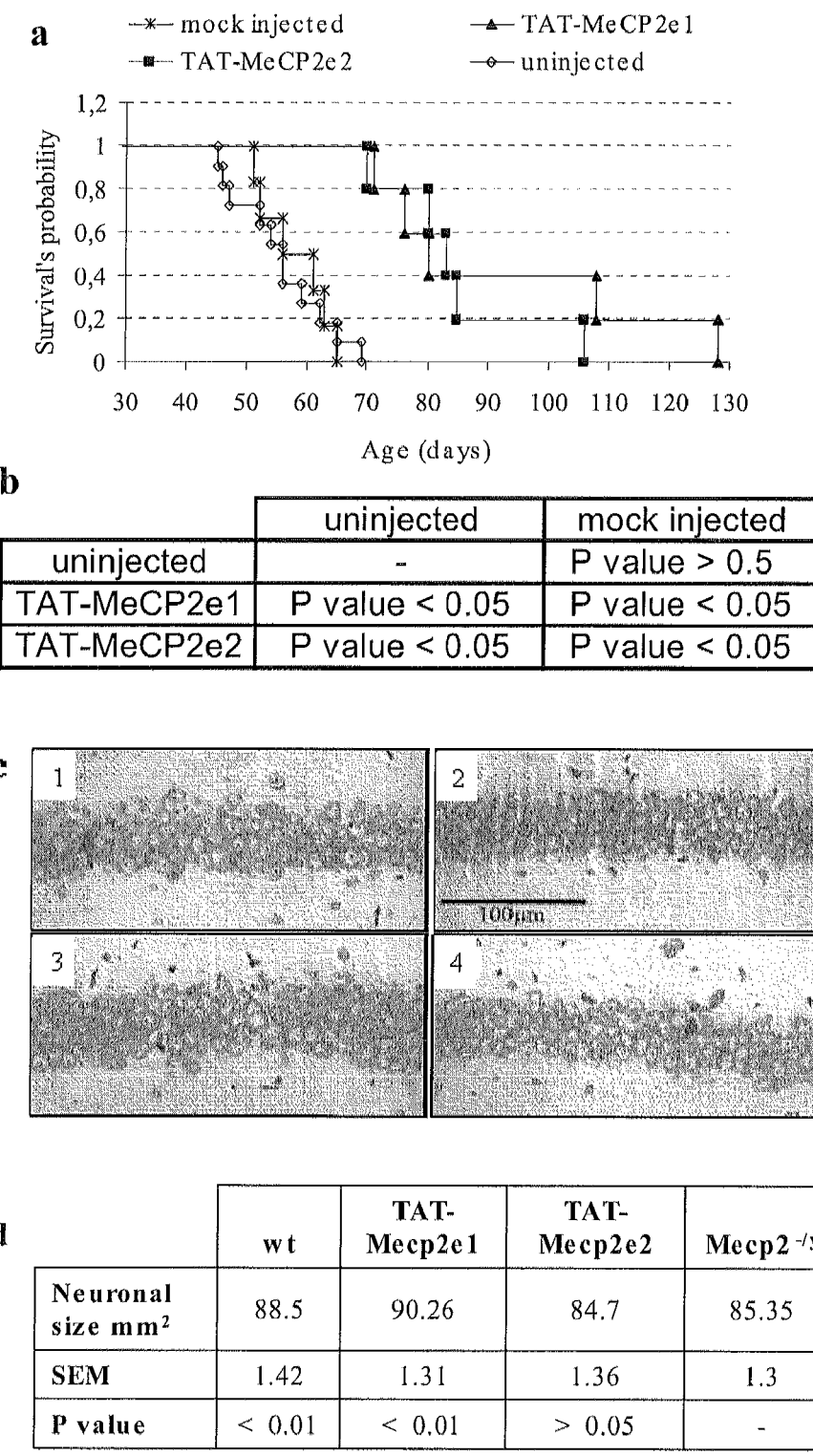

FIG. 8. Brain-delivered MeCP2 isoforms prolongs lifespan and rescues neuronal pathology in MeCP2$^{-/y}$ mice. a. Kaplan-Meier chart depicting the survival curves of MeCP2$^{-/y}$ mice untreated (n=11), mock treated (n=6) or treated with TAT-MeCP2e1 (n=5) or TAT-MeCP2e2 (n=5), respectively. b. The two tailed t-Student's test revealed a p value of <0.05 by an alpha value of 0.05 for both groups uninjected/mock injected versus TAT-MeCP2e1 and versus TAT-MeCP2e2. No statistically difference was present between the groups TAT-MeCP2e1/TAT-MeCP2e2 (p>0.8) as well as the uninjected/mock injected mice groups. c. Nissl staining of CA2 hippocampal neurons revealed smaller and more densely packed neurons in MeCP2$^{-/y}$ mice (1) compared to the wild-type mice (2). In contrast, TAT-MeCP2e1 (3) treatment reverted neuronal destruction in Mecp2$^{-/y}$ mice. In (4) is the image of the hippocampus of the mouse treated with TAT-MeCP2e2, which does not change the size of the neurons. d. Quantification of cellular rescue in hippocampal CA2 neurons (n=3 for wt, n=3 for Mecp2$^{-/y}$, n=4 for TAT-MeCP2e1 treated mice and n=3 for TAT-MeCP2e2).

EXEMPLIFYING SECTION

The following examples are meant to further illustrate, but not limit, the invention. The examples comprise technical features and it will be appreciated that the invention relates also to combinations of technical features presented in this exemplifying section.

1. Construct Generation

In order to establish whether a codon-optimized sequence will induce an improvement in the protein production, a two step strategy was used in planning the codon optimization. First, only about half of the coding sequence of the MECP2 was optimized, as described below, by selecting codons with frequency usage in the E. coli of at least 8-10%. Then, an evaluation of improved expression was performed. A significant increment of the protein yield with the "half synthetic" MeCP2 confirmed the validity of this strategy, and in a second step, the sequence was completely codon optimized, as illustrated in FIG. 3A. The overlapping region of the primers was typically of a length of 20 nucleotides with a melting temperature of typically at least 50° C., but in many cases longer overlapping regions had to be created in order to assure an efficient annealing during the PCR-mediated synthesis. A flow diagram for the generation of the following constructs is given in FIG. 2.

1. Two oligonucleotides complementary at their 3' end for 20 bases were designed (TAT-core-F and TAT-core-R, SEQ ID NO 7 and SEQ ID NO 8). Twenty pmol of each oligonucleotide were then elongated using Pfu polymerase (Stratagene, La Jolla, USA) at following conditions: 15 min denaturing at 96° C., followed by one elongation step at 60° C. for 30 min. The product was then cloned in the pBluescript vector (Stratagene, La Jolla, USA) and sequenced. Then two additional primers (TAT-new-F and TAT-new-R, SEQ ID NO 9 and SEQ ID NO 10) were used to amplify the previous insert generating a product with an EcoRI and HindIII restriction sites at the 5' and 3' genomic ends, respectively. This product digested with EcoRI and HindIII was then sub cloned into puc18 vector (Invitrogen, Karlsruhe, Germany) generating the pTAT-Strep construct. The cDNA encoding for the TAT and Strep tag-II contained in the pTAT-Strep construct is given in SEQ ID NO 5 (step 1, FIG. 2).

2. The EGFP cloning sequence was excised from the pEGFP-C1 vector (Clontech, Calif., USA) into the pTAT-Strep construct, named puc18-TAT-EGFP-Strep (step 2, FIG. 2).

3. The cDNA sequence of the MECP2 gene was amplified from the clone pCR-hMeCP2 (W. Strätling, Universitätsklinik Eppendorf, Hamburg, Germany) by Pfu polymerase using the primers NotI-3G-MeCP2-F and R-MeCP2-3G-NcoI (SEQ ID NO 11 and SEQ ID NO 12). The PCR product was tailored with sequences for NotI and NcoI restriction sites at the 5' and 3' genomic ends and cloned into puc18-TAT-EGFP-Strep. The derivative construct was the pTAT-MeCP2e2-EGFP-Strep (step 3, FIG. 2).

4. The pTri-EX-TAT-MeCP2e2-EGFP-Strep-His (step 4, FIG. 2) eukaryotic expression vector was generated by amplifying the TAT-MeCP2e2-EGFP-Strep sequence from the construct pTAT-MeCP2e2-EGFP sequence by Pfu polymerase using the BspHI-TAT-F (SEQ ID 38) and XhoI-EGFP-R (SEQ ID 39) primers. The PCR-product was digested by BsphI/XhoI and cloned into pTRI-Ex-Neo.1.1 vector (Novagen, Darmstadt, Germany) linearized with NcoI/XhoI.

5. A strategy similar to construct 1 was employed to generate the pET28-PTD4-6his construct using the oligonucleotides PTD4_core_F (SEQ ID NO 40), PTD4_core_R (SEQ ID NO 41), PTD4_amp_F (SEQ ID NO 42) and PTD4_amp_R (SEQ ID NO 43) generating a sequence encoding for the peptide PTD4 (Ho A et al. Cancer Res. 2001 Jan. 15; 61(2):474-7.) The resulting product was digested with NcoI and XhoI and cloned into the pET28a(+) vector similarly digested (Novagen, Merck, Darmstadt, Germany), generating the pET 28-PP4-6His plasmid (step 5, FIG. 2). The generated coding sequence contained in the pET 28-PP4-6His plasmid is given in SEQ ID NO 6.

6. The NdeI/BspeI fragment from the pTAT-MeCP2e2-EGFP-Strep was cloned into the pET28-PP4-6His digested with NdeI and AgeI. The resulting construct was named pET28-TAT-MeCp2e2-EGFP-6His. (step 6, FIG. 2)

7. A NotI/XhoI fragment from pTri-EX-MECP2-EGFP-Strep-6His was excided and cloned into the pET28-TAT-MeCP2e2-EGFP-6His digested with the same restriction endonucleases. The resulting construct was the pET28-TAT-MeCP2e2-EGFP-Strep-6His.

8. Part of the human sequence of MeCP2 was amplified using the Mecp2-His-F1 (SEQ ID 44) and Mecp2_His_rev (SEQ ID 45) primers. This product was cloned into pBluescript generating the pBlue-6His plasmid (step 8, FIG. 2).

9. The NdeI/DraI fragment containing the 6 His sequence and part of MeCP2 coding sequence was released from pBlue-fragment containing the His-tag and cloned into pET28-TAT-MECP2e2-EGFP-Strep-6His similarly digested. The generated plasmid was named pET28-6HisTAT-MeCp2e2-EGFP-Strep-6His (step 9, FIG. 2).

10. The XhoI and DraIII fragment from the pET28-6HisTAT-MeCp2e2-EGFP-Strep-6His was released from the vector. Then the same fragment but without the sequence encoding for the 6His sequence was amplified using the Mecp2_pet_XhoI (SEQ ID 46) and Mecp2_pet_DraIII (SEQ ID 47) primers. This PCR product was then used for reconstituting the fragment into pET28-6HisTAT-MECP2e2-EGFP-Strep-6His. The resulting plasmid was the pET28-6HisTAT-MECP2e2-EGFP-Strep (step 10, FIG. 2).

1.1 Generation of Synthetic Genes:

Attempts to produce recombinant protein using the pET28-TAT-MECP2e2-EGFP-Strep-His vector containing the human MECP2 EDNA were unsatisfying. The protein's yield was of about 0.1 mg/liter bacteria culture. In order to overcome this insufficient protein expression in *Escherichia coli*, a synthetic MeCP2 optimized for this specific organism was designed to circumvent the restrictions of the codons bias. The amino acid sequence of both isoforms e1 and e2 of the human MeCP2 was back translated according to the preferred codon usage of the *Escherichia coli*. The GC content of the cDNA sequences was also reduced, which may be an additional source of constraint for protein production. This artificial sequence was then created by PCR mediated synthesis using a series of overlapping nucleotides. We synthesized the MECP2e2 coding sequence in two separate reactions using Pfu Ultra high-fidelity DNA polymerase (Stratagene, La Jolla) with 18 complementary oligo-nucleotides. In a first step a set of 10 oligonucleotides (Seq ID NO 13 to SEQ ID NO 22) generated the sequence SEQ ID NO. 3 of 810 bp containing also the sequence encoding for the TAT domain and restriction sites for subcloning. The basic strategy for the synthesis is outlined in FIG. 1. In the first step, the two core oligonucleotides having 20 bp complementarity were annealed and extended. Further extension of the synthetic gene was carried out using the other complementary oligo-nucleotides with the generated PCR product as a template.

Reaction Components (for 50 μl):

| | |
|---|---|
| Primers: Tat_core_F/Tat_core_R (100 pmol/μl) | 1 μl each |
| dNTPs mix (2.5 mM each nucleotide/μl) | 8 μl |
| 10X DNA Polymerase buffer | 5 μl |
| Ultra Pfu DNA polymerase (2.5 Units/μl) | 2 μl |
| dd H2O | 33 μl |

Thermal Cycler Conditions for the First Fragment Generation:

First step: Initial Denaturation 96° C. for 30 sec; Followed by 10 cycles: 96° C. for 20 sec; 55° C. for 30 sec; 72° C. for 1 min;

Second step: 20 cycles: 96° C. for 30 secs; 72° C. for 1 min; Final extension at 72° C. for 5 min.

Figure 1:
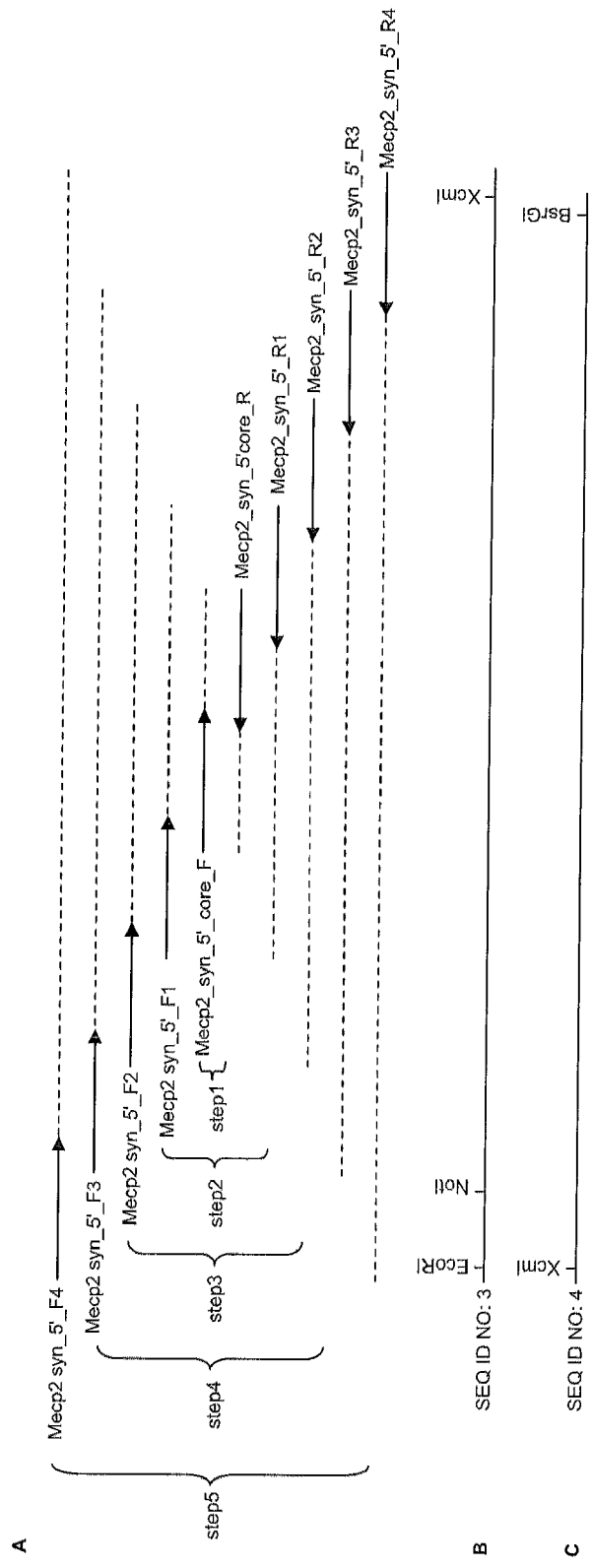
FIG. 1. A. The drawing shows the strategy for creating the synthetic sequence reported as SEQ ID NO: 3. Ten oligonucleotides have been designed according to the codons optimized sequence for *Escherichia coli* (arrows). The synthesis went on by a PCR reaction in step 1, creating a central fragment using two oligonucleotides of 100 bp in size complementary at their 3' end for 20 nucleotides (Mecp2_syn__5'_core_F and Mecp2_syn__5'_core_R). The end product was of 180 bp in size and is represented by the dashed elongated lines. An aliquot of this first product was then used as template for the second PCR reaction in step 2 using the two flanking oligonucleotides Mecp2syn__5'_F1 and Mecp2syn__5'_R1 each of 100 bp in size. The reaction was continued similarly in step 3, 4 and 5. B. The end product of the synthesis is represented along with three restriction sites used for subsequent cloning procedures. C. Schematic representation of the synthetic DNA generated by PCR with the relevant restriction sites used for cloning.

The resulting product was purified over the Montage (Millipore) PCR clean-up column. For the subsequent reaction steps, 1 μl of the purified PCR product and 10 pmol of each of following primer pairs were used at the following conditions: initial denaturation 96° C. for 2 min followed by 25 cycles at 96° C. for 20 sec; 55° C. for 30 sec; 72° C. for 1 min. Each following amplification step was performed at the same conditions using as input DNA the previously generated fragment by incrementing the extension time with 10 sec for further amplification steps (FIG. 1).

11. The generated sequence was cloned into the pBluescript and checked for sequence errors. One clone free from errors was selected and named pBlue-MECP2 e2-syn (step 11, FIG. 2).

12. The EcoRI/XcmI fragment was released from pBlue-MECP2 e2-syn and cloned into pTAT-MECP2e2-EGFP-Strep previously digested with the same restriction enzymes. The resulting plasmid was named pTAT-MECP2 e2 syn-EGFP-Strep (step 12, FIG. 2).

13. A NotI/SacI fragment from pTAT-MECP2 e2 syn-EGFP-Strep was released and cloned into pET28-6His-TAT-MECP2-EGFP-Strep similarly digested. The resulting plasmid was the pET28-His-TAT-MECP2 e2(half)syn-EGFP-Strep (step 13, FIG. 2).

14. The EGFP was released from the pET28-His-TAT-MECP2 e2(half)syn-EGFP-Strep vector by digestion with Sac II and BsrGI. A PCR product generated using reverse primer Mecp2_BsrGI (SEQ ID NO 31) and forward primer Mecp2_128_1306 (SEQ ID NO 32) regenerating the partly deleted MeCP2, was produced and cloned into the SacII/BsrgI restriction sites of pET28-His-TAT-MECP2 e2(half) syn-EGFP-Strep. The resulting vector was named pET28-His-TAT-MECP2 e2(half)syn-Strep, which is not encoding for EGFP (step 16 FIG. 2).

A second set of 8 oligonucleotides (SEQ ID NO 23 to SEQ ID NO 30) was employed to generate the sequence SEQ ID NO 4 using a similar strategy depicted in FIG. 1 and above.

15. The PCR product was cloned into pBluescript and was named pBlue-MECP2 e2-syn_3part (step 14, FIG. 2).

16. The XcmI/BsrGI from pBlue-MECP2 e2-syn_3part was released from the vector and cloned into pTAT-MECP2 e2 syn-EGFP-Strep generating the pTAT-MECP2 e2 syn. This vector contains the completely optimized sequence shown in SEQ ID NO 2 (step 15, FIG. 2).

17. The complete synthetic MeCP2e2 sequence contained in pTAT-MECP2 e2 syn was excised with NotI/BsrGI and cloned into pET28-His-TAT-MECP2 e2(half)syn-Strep similarly digested. The resulting fragment contains the complete synthetic sequence of MeCP2 and was called pET28a-6His-TAT-MECP2 e2 syn-Strep, which is one of the construct used for large scale protein production.

18. A PCR product was generated with the oligonucleotides using Mecp2b_syn_F(SEQ ID NO 33), Mecp2b_syn_core (SEQ ID 34) and Mecp2b_syn_R (SEQ ID 35) containing the sequences of the isoform MeCP2e 1.

Reaction Components (for 50 μl):

| | |
|---|---|
| Primers: Mecp2b_syn_core/Mecp2b_syn_R (100 pmol/μl) | 1 μl each |
| dNTPs mix (2.5 mM each nucleotide/μl) | 8 μl |
| 10X DNA Polymerase buffer | 5 μl |
| Ultra Pfu DNA polymerase (2.5 Units/μl) | 2 μl |
| dd H2O | 33 μl |

Thermal Cycler Conditions for the First Fragment Generation:
first step: Initial Denaturation 96° C. for 30 sec; followed by 10 cycles: 96° C. for 20 sec; 55° C. for 30 sec; 72° C. for 1 min;
Second step: 20 cycles: 96° C. for 30 secs; 72° C. for 1 min; final extension at 72° C. for 5 min.

One μl from the generated PCR fragment was used as input DNA for the following reaction:
Reaction Components (for 50 μl):

| | |
|---|---|
| Primers: Mecp2b_syn_F/Mecp2b_syn_R (10 pmol/μl-) | 1 μl each |
| One μl PCR product from first PCR | 1 μl |
| dNTPs mix (2.5 mM each nucleotide/μl) | 8 μl |
| 10X DNA Polymerase buffer | 5 μl |
| Ultra Pfu DNA polymerase (2.5 Units/μl) | 2 μl |
| dd H2O | 32 μl |

Initial Denaturation:
96° C. for 1 min
Followed by 30 cycles at following conditions:
96° C. for 20 sec; 60° C. for 30 sec; 72° C. for 30 sec
Final extension step: 72° C. for 5 min.

Figure 2:
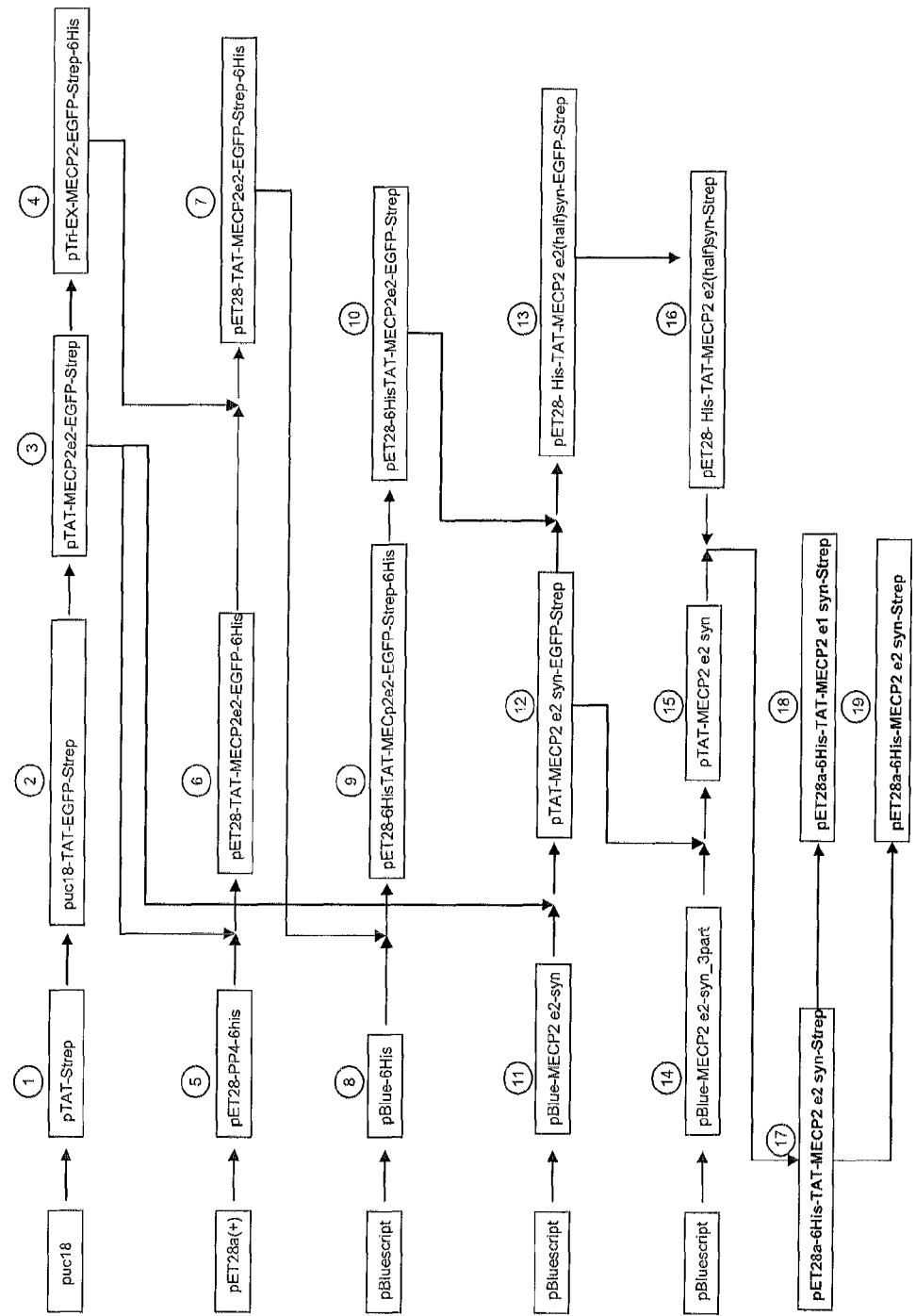
FIG. 2. Flow diagram for the generation of MECP2 constructs. The flow shows the cloning procedures with all the intermediate steps leading to the final expression vectors containing the synthetic genes for MeCP2e1 and MeCP2e2 fused with the TAT domain.

This PCR fragment replaced the fragment from the EagI to the PstI sites of the pET28a-6His-TAT-MECP2e2syn generating the pET28a-6His-TAT-MECP2e1syn Strep (step 18, FIG. 2).

19. A PCR product generated by using the primers Mecp2-syn-Nde I_F (SEQ ID 36 and Mecp2-syn-BsrG I_R SEQ ID 37) amplified the complete MECP2 synthetic sequence but without the TAT domain was then cloned into pET28-His-TAT-MECP2 e2(half)syn-Strep similarly digested. The resulting plasmid was named pET28a-6His-MECP2 e2 syn-Strep (step 19, FIG. 2).

2. Expression and Purification of the Proteins

Crucial steps in this study were to achieve an efficient production of recombinant proteins. As outlined above, we created a synthetic MECP2-cDNA sequence for both isoform e1 and e2 according to the *Escherichia coli* codon-usage to increase the yield of recombinant proteins (FIG. 3A). Several in vitro investigations shown below, demonstrated the biochemical activity of the TAT-MeCP2 fusion isoforms despite the presence of additional domains (see also FIG. 5 and FIG. 7). In contrast to the most common strategy to extract proteins fused with transduction domains under denaturing conditions, we decided to extract recombinant proteins under native conditions in order to retain completely their functional activity and to reduce the intracellular degradation due to misfolding. The in vitro experiments showed below pointed out that also these natively extracted proteins have high transduction efficiency.

For protein expression, *Escherichia coli* strain Rosette 2 (DE3) (Novagen) was transformed with plasmid vectors through electroporation. A single colony was inoculated into 10 ml LB supplemented with 50 μg/ml kanamycin and grown overnight at 37° C. with shaking. The preculture was diluted 1:25 and grown in 250 ml LB supplemented with 50 μg/ml kanamycin, for 5 hours at 37° C. and later kept at 4° C. for one hour. The culture was further diluted 1:10 in 2.5 Liters rich media (2.5 g meat extract per liter of LB), supplemented with 50 μg/ml kanamycin and induced with 1 mM IPTG for about 12 hours at 30° C. The cells were collected by centrifugation at 7000 g for 10 min, 4° C. The pellet was resuspended in bacterial lysis buffer (15 ml/l culture pellet) with 100 μg/ml PMSF, 1 μl/ml Protease inhibitor cocktail (CALBIOCHEM), Lysozyme 500 μg/ml, 1 Unit/ml Benzonase (Merck Biosciences) and lysed by vortexing. The lysate was incubated at room temperature for 10 minutes, then on ice for 15 minutes before being subjected to ultra-sonication (50-60 secs duty cycles, 5-6 output) 6 times, 1 minute each with an interval of 2 minutes to avoid heat. The lysate was centrifuged at 18,000×g for 25 min, 4° C., then the supernatant was filtered using 0.45 μM filters (Millipore) and purified over streptactin affinity columns (IBA, Goettingen, Germany) using the suppliers protocol. The protein was then subjected to a buffer exchange using the PD-10 desalting columns (GE Healthcare, Freiburg, Germany). The buffer composition was: 20 mM HEPES, 300 mM NaCl, 0.1 mM $CaCl_2$ and 10% gylcerol. The bacterial lypopolysaccharides have been removed by EndoTrap columns (Profos, Regenburg, Germany) according to the supplier's protocols after equilibrating the columns with the previously described buffer.

3. Cell Culture and Transduction of Fusion Proteins 3.1 Cell Lines

NIH3T3 cells (Mouse fibroblast, ATCC CCL 92) were cultured in Dulbecco's modified Eagles medium (PAN Biotech), containing 10% fetal bovine serum (PAN Biotech) and antibiotics penicillin (100 U/ml), streptomycin (100 μg/ml) (PAN Biotech) at 37° C. with 5% $CO_2$.

Fibroblasts from a female Rett patient skin biopsy, carrying one of most frequent mutation of the MECP2 gene (T158M) were cultured in RPMI 1640 with 15% fetal calf serum, penicillin (100 U/ml), streptomycin (100 μg/ml) and L-glutamate (100 ng/ml) at 37° C. with 7% $CO_2$.

Fibroblasts from $Mecp2^{-/y}$ mice were established from postnatal day 7 (P7), using hind limb/tail tip. The tissue was rinsed with DPBS and minced into small pieces with a sterile scalpel in 35 mm dish containing media under laminar air flow. Carefully the media was aspirated and replaced with new media and the dish was incubated for a week without changing the media at 37° C. with 10% $CO_2$, further the fibroblasts cells were maintained in Dulbecco's modified Eagles medium, containing 20% fetal bovine serum and antibiotics penicillin (100 U/ml), streptomycin (100 μg/ml) at 37° C. with 7% $CO_2$.

The brain of postnatal day 7 (P7) pups dissected under laminar flow, was used to isolate the hippocampus and cerebral cortex for neuronal culture according to a published protocol (Ray, J., et al., 1993, PNAS 90:3602-6).

3.2 Establishment of Stable Cell Lines Expressing TAT-MeCP2e2-EGFP Protein

To establish stable cell lines expressing TAT-MeCP2-EGFP, we used NIH3T3 (mouse fibroblasts) and HeLa cells (human cervical carcinoma). HeLa cells were cultured in MEM-alpha (PAN Biotech, Aidenbach, Germany), with 10% fetal calf serum, penicillin (100 U/ml), streptomycin (100 μg/ml), and L-glutamate (100 ng/ml). NIH3T3 were cultured in DMEM with 10% fetal calf serum, penicillin (100 U/ml), streptomycin (100 μg/ml). Cells were transfected with pTriEx-TAT-MeCP2e2-EGFP-Strep-His using Gene juice transfection reagent according to suppliers protocol (Novagen). Two days post transfection, cells were selected on medium containing 500 μg/ml neomycin (GIBCO) for 6 weeks and maintained thereafter on medium with 200 μg/ml neomycin. The pictures were taken by growing cells for a day in two chamber culture slides (Falcon, BD bioscience, Heidelberg, Germany). The cells were washed and mounted with Vector shield mounting medium containing DAPI (Vector laboratories, Burlingame, Calif.) and the distribution of the fluorescence was analyzed on an Olympus microscope BX60 (Olympus Optical Co. LTD, Japan) at 200× magnification in five different fields using the SIS analysis software (Soft Imaging System GmbH, Munster).

3.3 Establishment of Rett Patient's Monoallelic Primary Cell Line

The patient's fibroblasts were transfected with the plasmid pCI-neo-hTERT plasmid (Counter, C. M. et al., 1998, Oncogene 16:1217-22 and Lundberg, A. S. et al., 2002, Oncogene 21:4577-86) containing hTERT (Human Telomerase Reverse Transcriptase Subunit) encoding gene using SuperFect transfection Reagent according to supplier's (Qiagen, Hilden, Germany) protocol. The transfected cells were selected for 6 weeks in G418 (200 µg/ml) (Calbiochem, San Diego, USA) containing media and maintained thereafter on medium with 100 µg/ml G418. To establish a monoallelic expressing cell line, cells were trypsinized and diluted with media, single cells were micro-pipetted under direct microscope visualization, individual cells were transferred to 24 well plates containing filtered conditioned medium from exponentially growing primary cells supplemented with 20 ng/ml bFGF (basic Fibroblast Growth Factor) (Sigma, Deisenhofen, Germany). Upon confluence of the well, the cells were trypsinized and expanded. The total RNA was extracted using RNeasy kit (Qiagen, Hilden, Germany) and cDNA was synthesized using Superscript-II Reverse Transcriptase and Oligo (dT) 12-18 primer (Invitrogen). The region containing the mutation was analyzed by RT-PCR using flanking primers (Rett_EX3-F and Rett_EX4-R, SEQ ID NO 48 and SEQ ID NO 49). The clonality was confirmed by sequence analysis of RT PCR products.

4. Transduction of Fusion Proteins and Analysis of Transduced Cells

For the transduction of TAT-MeCP2-EGFP and EGFP proteins, cells were grown to confluence in two chamber culture slides (Falcon, BD Bioscience, USA). The cultures were supplied with fresh medium and were then treated with various concentrations of fusion proteins (500-1500 pmol/ml) for different intervals of time. The transduction of TAT-MeCP2e1 and TAT-MeCP2e2 as well as MeCP2 proteins was carried out after labelling them with NHS-rhodamine labelling according to the manufacturer's protocol (Pierce biotechnology, IL, USA), followed by gel filtration on a PD-10 column to remove the unincorporated rhodamine. To visualize the distribution of the fluorescence, the cells were washed gently with cold PBS and fixed in freshly prepared 4% paraformaldehyde in PBS for 5 min at RT. The cells were washed again with PBS before being mounted with Vector shield mounting medium containing DAPI (Vector laboratories, Burlingame, Calif.) and the distribution of the fluorescence was analyzed under a fluorescent microscope BX-60 (Olympus Optical Co. LTD, Japan) at 200× magnification in five different fields using the analySIS software (Soft Imaging System GmbH, Munster) and also confocal images were taken on a Leica TCS SP2 AOBS laser scan microscope.

Figure 3:
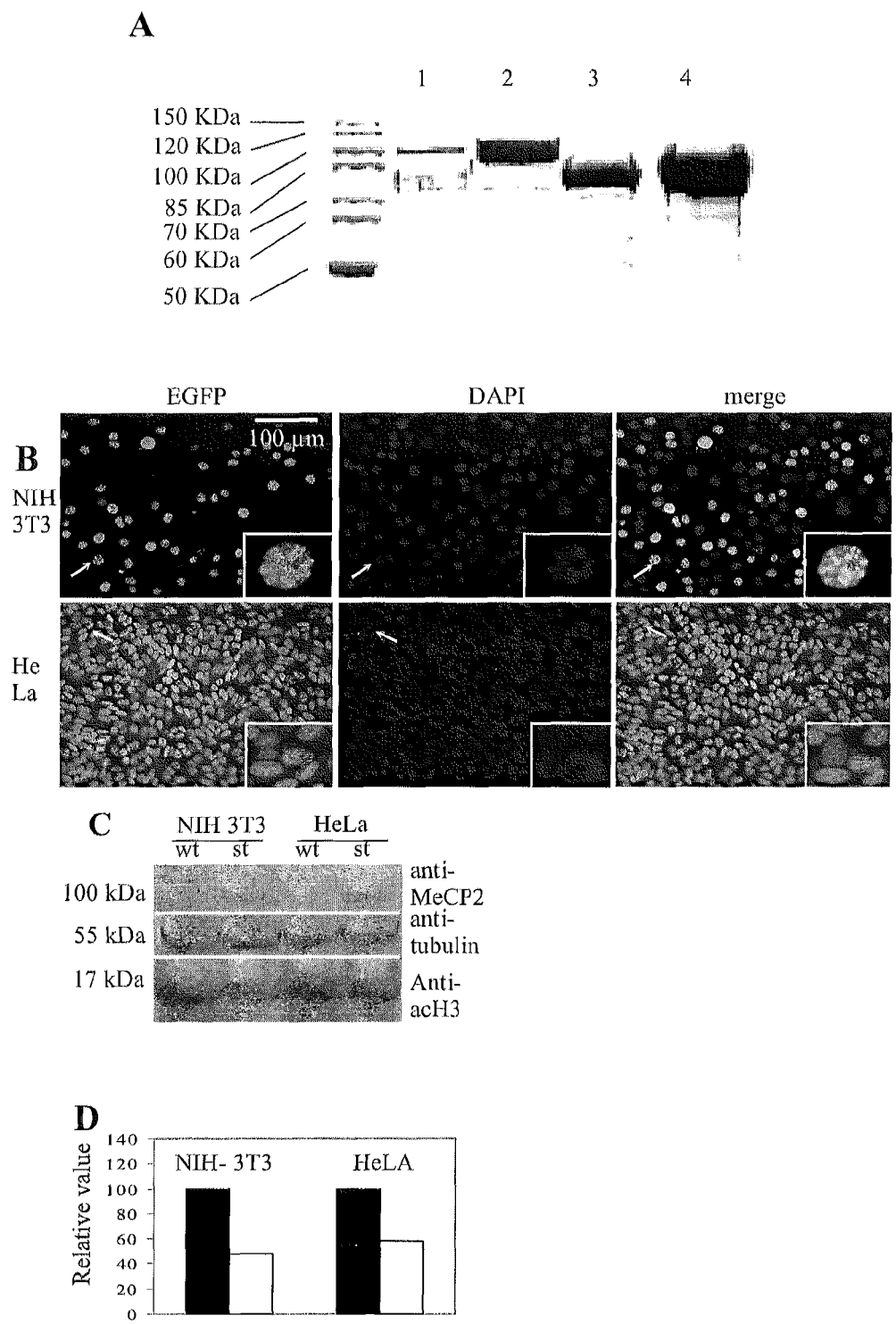
FIG. 3. A. Increment of MeCP2e2 protein produced by optimizing the sequence according to the *Escherichia coli* codon usage. Strep-tagged recombinant fusion proteins were separated on 10% SDS-PAGE and stained with Coomassie blue. The protein amount loaded on the gel corresponds to an equal quantity of processed liquid culture of bacteria. Lane 1, TAT-MeCP2e2-EGFP from human cDNA; lane 2, TAT-hsMeCP2e2-EGFP from a MeCP2 cDNA sequence partially optimized for *E. coli* codon usage. Lane 3, His-TAT-hs-MeCP2 from a MeCP2 cDNA sequence partially optimized for *Escherichia coli* codon usage. Lane 4, His-TAT-sMeCP2 produced from complete synthetic MECP2 gene. The picture clearly shows a strong increment of the protein yield using the codon optimized cDNA sequence.

5. Creation of Cell Lines Stably Overexpressing the Mecp2E2 Protein and Successful Transduction of Primary Cells We established HeLa and NIH3T3 cell lines stably expressing the TAT-MeCP2e2-EGFP fusion protein tagged at the C-terminus with the Strep-II and 6-His affinity tags by using the pTri-Ex-MECP2-EGFP-Strep-His construct. After transfection of cells with this construct, the protein was predominantly localized in the heterochromatic regions of the nucleus, as particularly evident for the mouse NIH3T3 cell line (FIG. 3B). Particularly in the NHI3T3 cells we detected a strong reduction of histone H3 acetylation that is known to be mediated by MeCP2 (FIGS. 3 C and D). These results point out that the TAT-MeCP2e2-EGFP protein is functionally active, irrespective of the additional protein domains, which were introduced.

We created a series of constructs to express both isoforms of MeCP2 with and without the EGFP protein at the C-terminus and fused at the N-terminus with the TAT domain (FIG. 2). Further constructs contained a synthetic MECP2 gene completely codon-optimized for *Escherichia coli*. The usage of the synthetic MECP2 cDNA sequence increased the protein production in *E. coli* of up to 200-fold. (FIG. 3A). We tested the delivery of the TAT fusion proteins and found the highest efficiency in vitro at 500 pmoles of recombinant proteins. After three hours of incubation with the TAT-MeCP2e2-EGFP protein, about 40% of the NIH 3T3 cells showed the presence of gross vesicle-like fluorescent spots. The protein was mostly in the cytosol (FIG. 4A a, b). After 12 hours, nearly 100% of the cells were fluorescent (FIG. 4A c, d) and the protein was concentrated in the nuclei of the cells (FIG. 4A e). Transduction was stable for 24 hours in transduced cells (FIGS. 4 B and C). Experiments using the protein EGFP without a TAT domain as control did not result in any uptake into the cells (FIG. 4A f). The TAT-recombinant proteins were also able to transduce human primary fibroblasts (FIG. 4A g and h) and primary neurons from mouse brain (FIG. 4A i and j).

6. MeCP2 can be Substituted in Fibroblasts Derived from a Patient with RTT Syndrome and in Murine Mecp2$^{-/y}$ fibroblasts.

We then studied the biological activity of the MeCP2 fusion proteins after delivery into MeCP2 deficient cells. We detected a hyperacetylation of the histones H3 and H4K16 in monoclonal cell lines expressing a mutated MeCP2 allele (T158M) in contrast to cell line expressing the wild type allele (FIG. 5 a). A cell line expressing the mutated allele was treated with 300 pmol of TAT-MeCP2e1 TAT-MeCP2e2, MeCP2, or TAT-EGFP proteins for 64 hours. A reversion of the hyperacetylation of histones H3 and H4K16 was observed only after treatment with both TAT-MeCP2 isoforms (FIGS. 5 a and b). We have got similar results targeting fibroblasts of Mecp2$^{-/y}$ mice (FIG. 5 c). Communoprecipitation experiments in transduced fibroblasts of Mecp2$^{-/y}$ mice directly demonstrated the recruitment of histone deacetylase 1 (HDAC1) by the TAT-MeCP2 isoforms (FIG. 7A). These results prove that TAT-MeCP2 isoforms are able to rescue the biochemical changes caused by a loss of function of the endogenous MeCP2.

7. Intracellular Stability of the TAT-MeCP2 Proteins

To examine the stability and persistence of the transduced protein in the cells, the cells were incubated for 2 hours with 1 nmol of TAT-MeCP2e1 and TAT-MeCP2e2 separately. They were then washed with media and incubated with new culture media for further growth. The cells were harvested at indicated time intervals and proteins were extracted by suspending 10$^7$ cells in 200 µl cell lysis buffer (125 mM Tris-HCl pH 6.8, 2% SDS, 50 mM NaH2PO4, 20% glycerol, 1 mM DTT, 1 mM PMSF) and incubating on ice for 20 min, sonicating gently to fragment the DNA. The lysate was centrifuged at 9000×g for 10 min. 4° C., and the total protein concentration of the supernatant was quantified using Bradford method and stored at −80° C. until use. 100 µg of the protein samples were heated at 75° C. with 4×SDS loading buffer (1 M Tris-HCl pH-6.8, 2% SDS, 0.02% bromophenol blue, 5 mM beta-2-mercaptoethanol, 5% glycerol) and resolved on 4-20% precise protein gels (Pierce Biotechnology, USA). The proteins were transferred to nitrocellulose membrane optimized for protein transfer (Amersham Biosciences, GE Healthcare). The membrane was treated with Western Blot signal enhancer (Pierce Biotechnology, USA) following supplier's protocol. The membrane was blocked with 5% non-fat milk in PBS with 0.05% Tween-20 (PBS-T) for 1 hr. Then the membrane was incubated separately with blocking solution containing MeCP2 antibody (Upstate, USA) diluted 1:2,000 for overnight at 4° C. Mouse monoclonal anti-alpha tubulin (Sigma, Taufkirchen, Germany) diluted 1:4,000 was used as a positive control. The membrane was washed 3 times for 5 minutes each with PBS-T and then incubated with same buffer containing respective secondary antibodies conjugated with Alkaline phosphatase (Sigma) diluted 1:30,000 for 1 hr. Excess of antibodies was washed off with PBS-T three times and developed with BCIP/NBT (Carl-Roth, Germany). The intracellular concentration of the transduced protein remained high for 24 hours after which the level decayed to less than a quarter of the starting concentration over the next 24 hours (FIGS. 4B and C).

8. Western Blot Analysis 8.1 Cell cultures protein extracts: Total protein content from all cell lines and primary fibroblasts cell cultures was extracted by suspending $10^7$ cells in 200 µl cell lysis buffer and incubated on ice for 20 min, sonicated gently to fragment the DNA. The lysate was centrifuged at 9000×g for 10 min, 4° C. Western Blot was done as described above. The membrane was incubated overnight at 4° C. separately with blocking solution containing rabbit polyclonal antibodies against histone-H3 at a dilution of 1:4,000, acetylated histone H3, acetylated histone H4K16 (Upstate) diluted 1:10,000 and 1:500 respectively. Mouse monoclonal anti-alpha tubulin (Sigma) diluted 1:4,000 was used as a positive control.

8.2 Tissue protein extracts: Mice were injected with 100 µg/g (body weight) TAT-MeCP2-EGFP, TAT-MeCP2 and MeCP2. After 20 hours the mice were killed. The brain was removed and washed in cold PBS. The brain was then homogenized in extraction buffer (62 mM Tris-Cl pH 6.8, 2% SDS, 5 mM Mercaptoethanol, 0.15 mM NaCl), 5× protease inhibitor cocktail (Sigma)) and sonicated gently. The lysate was pelleted down at 15,000×g for 15 min, 4° C. Fifty µg was employed for the Western blotting carried out as mentioned above using a polyclonal anti-MeCP2 antibody (Upstate). In independent experiments, we injected mice with 100 µg/g (body weight) of TAT-EGFP and of TAT-MeCP2e2-EGFP. The immunoblotting was done on total protein extract from the brain, liver, kidney and heart using anti GFP antibody (Sigma). The density of the Western Blot signals was quantified by Olympus S-100 Imaging Densitometer. Band intensity ratios were measured using alpha-tubulin signal as an internal control.

9. Immunohistochemistry

Mice injected i.p. with TAT-MeCP2e2-EGFP and EGFP were transcardially perfused with cold 4% paraformaldehyde (PFA) in PBS buffer 20 hours post injection. Brains were removed and postfixed with (4% PFA) for 4 hours, cryoprotected with 30% sucrose at 4° C. and stored at −80° C. Immunohistochemistry was performed on cryosections using rabbit anti-GFP antibody (Sigma). Images were taken with Olympus microscope BX60 (Olympus Optical Co. LTD, Japan). Analogous experiments were performed on formalin-fixed slice of Mecp2$^{-/y}$ mice injected for 20 days with TAT-MeCP2e1 and e2 (20 µg/g body weight, each second day). The slices were probed with a polyclonal rabbit anti-MeCP2e2 antibody. This antibody has been established in rabbit using the human recombinant protein MeCP2e2.

10. Protein Therapy In Vitro and In Vivo 10.1 In Vitro Protein Therapy

We have tested the recombinant proteins in monoalleleic cell lines expressing the T158M MeCP2 mutation. These cells show a hyperacetylation of H3 and H4K16. The incubation with both TAT-MeCP2e1 and e2 isoforms reverted the pathological hyperacetylation into a level similar to the wild type cell lines (FIG. 5).

10.2 Efficient Delivery of Mecp2 Proteins into the Brain

We then addressed the question of protein delivery in vivo in NMRI wild type mice receiving one single intraperitoneal injection of TAT-MeCP2e2-EGFP, TAT-EGFP, or EGFP protein (60 µg/g body weight in PBS/10% glycerol or 20 mM HEPES/10% glycerol). The mice injected with TAT-EGFP and EGFP did not develop any apparent side effects. However, mice injected with TAT-MeCP2e2-EGFP isoform showed a transient hypomobility of the hind limbs, which disappeared one to two hours after the injection. Western Blot analysis of the brain, liver and kidney revealed the uptake of TAT-EGFP and TAT-MeCP2-EGFP proteins 20 hours after the injection (data not shown). In analogous experiments, mice were injected at the dosage of 100 µg/g body weight-independently with TAT-MeCP2e2, TAT-MeCP2e2-EGFP and MeCP2e2 proteins. The western blot analysis revealed the presence of the TAT-recombinant proteins in the brain extracts of the mice sacrificed 20 hours after injection (FIG. 6 a). Immunohistochemistry of brain slices using an anti-EGFP antibody revealed the presence of the TAT-MeCP2e2-EGFP protein in pyramidal neurons of the neocortex, in the cerebellar granule cell neurons, and in the meninges (FIG. 6 b). However, by increasing the dosage of both TAT-MeCP2 isoforms up 130 µg/g body weight we observed the development of severe side effects such as seizures-like symptoms within 10 to 20 minutes post-injection that resulted in a complete paralysis of all four limbs. As a consequence, two out of 5 injected NMRI mice died within 2 hours. In contrast, mice injected with TAT-EGFP and MeCP2 proteins did not have any serious side effects at any tested dosage (Table 1 below). These data indicate that successful delivery of MeCP2 proteins to the brains is in principle possible, however, the dosage has to be tightly controlled.

In the next series of experiments, we determined the delivery of MeCP2 fusion proteins to the brain of Mecp2-deficient mice, a Rett mouse model created in the laboratory of A. Bird (Chen et al. 2001, Nat Genet, 27 (3):327-31). The animals were purchased from the Jackson Laboratory, USA (strain B6.129P2(C)-Mecp2tm1.1Bird/J), and further breeding was done in the animal facility of the Institute of Human Genetics, Göttingen. Control mice were taken from the above mentioned animal facility. Two Mecp2$^{-/y}$ mice were injected i.p. for 20 days with 20 µg/g body weight each second day with TAT-MeCP2e1 and TAT-MeCP2e2, respectively. Similar as in wild-type mice, we could detect the TAT-MeCP2 proteins by immunohistochemistry on brain slices of Mecp2$^{-/y}$ mice (FIG. 6 c). These experiments prove that the TAT fusion proteins cross the blood-brain barrier and reach the brain. At the therapeutic regime of 20 µg/g body weight each second day, we never observed any immediate or delayed neurological symptoms or sudden death of the treated Mecp2−/y mice. The injection buffer for intraperitoneal delivery was 20 mM Hepes, 100 µM CaCl$_2$, 300 mM NaCl and 10% glycerol.

10.3 In Vivo Protein Therapy: Therapeutic Effects of the Recombinant TAT-MeCP2 Isoforms in a Mouse Model of Rett Syndrome Next we tested whether the in vivo delivered MeCP2 proteins are functionally active in the brain of MeCP2-deficient mice. We injected daily i.p. TAT-MeCP2e1 or TAT-MeCP2e2 in Mecp2$^{-/y}$ mice at a dosage of 20 or 30 µg/g, respectively. At these dosages no clinical side effects were apparent. The animals were sacrificed after two weeks of therapy and total protein extracts from the brain were analysed by Western Blot. The injection of 20 or 30 µg/g of protein notably reduced the level of H4K16 acetylation (FIG. 7 B and C). After having demonstrated biochemical activity of the in vivo delivered proteins, we wanted to assess whether the therapy could rescue the phenotype of MeCP2-deficient mice. We injected Mecp2$^{-/y}$ mice i.p. with 20 µg/g body weight using both TAT-MeCP2 isoforms. Five Mecp2$^{-/y}$ mice received the TAT-MeCp2e1 and five the TAT-MeCP2e2. One Mecp2$^{-/y}$ mouse was injected with PBS, one mouse with MeCP2 and 4 mice received TAT-EGFP protein at the same dosage. Eleven Mecp2$^{-/y}$ mice were not treated and served as further controls. The treatment started at postnatal day 30. The average survival of the MeCP2-injected Mecp2$^{-/y}$ mice (n=10) was 88.7 days (92.6 for e1 and 84.8 for e2 isoform, respectively), of untreated Mecp2$^{-/y}$ mice 55.6 days and of the mock injected 57.0 days (Table 2 below). This represents an increase of the lifespan of almost 66% (TAT-MeCP2e1) and 53% (TAT-MeCP2e2) of the treated mice versus untreated ones. The survival prolongation is statistically highly significant (FIGS. 8 a and b). One wild type male mouse treated for three months with 20 µg/g MeCP2 did not develop any clinical side effects and was still healthy at 300 days of treatment.

TABLE 1

Effect of high dosage of recombinant proteins in wild type mice

|  | MeCP2e1 n = 3 | TAT-MeCP2e2 n = 3 | TAT-MeCP2e2-EGFP n = 3 | TAT-EGFPa n = 5 | EGFPa n = 3 |
|---|---|---|---|---|---|
| One hour post injection | Normal | Seizure and paralysis of hind limbs | Seizure and paralysis of hind limbs | unspecifically physical discomfort | Normal |
| Twenty four hours post injection | Normal | Slightly recovered* | Slightly recovered* | Normal | Normal | a. All proteins were injected at the dosage of 130 μg/g body weight. The TAT-EGFP and EGFP proteins contained due to the lower molecular weight approximately the double number of molecules as the TAT-MeCP2 proteins.
*In 2 experiments the mice died. A dosage of 30 μg/g of recombinant proteins did not have any particular effect on the mice irrespective of which protein was injected.

TABLE 2

Survival in days of injected and control Mecp2$^{-/y}$ mice

| uninjected | Mock injected | TAT-MeCP2e1 | TAT-MeCP2e2 |
|---|---|---|---|
| 45 | 52 (a) | 71 | 70 |
| 46 | 61 (b) | 76 | 80 |
| 47 | 51 (c) | 80 | 83 |
| 52 | 56 (c) | 108 (d) | 85 |
| 54 | 57 (c) | 128 | 106 |
| 56 | 65 (c) | | |
| 56 | | | |
| 59 | | | |
| 62 | | | |
| 65 | | | |
| 69 | | | |
| Average 55.5 | Average 57 | Average 92.6 | Average 84.8 |

(a) Injected with PBS
(b) Injected with MeCP2
(c) injected with TAT-EGFP
(d) This animal was still mobile and active but was killed because of a very severe and untreatable skin infection causing a mutilating self biting behaviour.

11. TAT-MeCP2 Protein Delivery Rescues Neuronal Damage In Vivo

It has been described that deletion of MeCP2 in postnatal CNS neurons lead to severe neuropathological changes, such as alterations in dendritic processes and neuronal shrinkage (Armstrong DD. 2002, Ment Retard Dev Disabil ResRev 8:72-6). In order to investigate whether treatment with TAT-MeCP2 protein also protects neurons from morphological changes, neurons from hippocampus and cerebellum were examined histologically. Neuronal size was assesed quantitatively in Niss1-stained sections (FIG. 8c) in the hippocampal CA2 region or on Calbindin stained cerebellar Purkinje cells. Mutant neurons in the hippocampus were smaller in size and were more densely packed than wild-type neurons (FIG. 8c, 1 and 2). Importantly, MeCP2-treated animals showed larger neurons without any apparent morphological changes (FIG. 8c 3). Quantification revealed that neuronal size was indistinguishable in TAT-MeCP2e1 treated hippocampal neurons compared to wild-type, whereas MeCP2e2 isoform had no effect on neuronal size (FIG. 8c 4). Measurements of pyramidal cortical neurons of the layer V in MeCP2-deficient mice of 50 days of age showed no differences to the wild-type situation. In addition, cerebellar Purkinje cells were preserved in MeCP2$^{-/y}$ mice and showed no gross morphological abnormalities after TAT-MeCP2 treatment (data not shown). Taken together, reduction of neuronal size in the hippocampus could be reversed by application of MeCP2e1.

The invention claimed is:

1. A method of treating Rett syndrome,
comprising the step of administering a pharmaceutical composition comprising
(i) a human MeCP2 protein or biologically active fragment of said human MeCP2 protein, or a derivative of said protein or fragment, and
(ii) a protein transduction domain, wherein the MeCP2 protein is fused to the protein transduction domain,
to a subject suffering from Rett syndrome,
wherein said fragment comprises at least 150 contiguous amino acids of the MeCP2 protein; and wherein said derivative of said protein or fragment has at least 60% sequence identity with the amino acid sequence of the MeCP2 protein or fragment thereof; and wherein said fragment or said derivative has at least 60% of the biological activity of the naturally occurring MeCP2 protein in a transcription assay which measures the ability of a protein to bind methylated cytosines.

2. The method of claim 1, wherein the MeCP2 protein or biologically active fragment or derivative thereof is selected from the group consisting of human MeCP2 isoform e1 as encoded by SEQ ID NO: 1 or human MeCP2 isoform e2 as encoded by SEQ ID NO: 2, or a biologically active fragment of any one of said isoforms, and a derivative of said isoforms or said fragments.

3. The method of claim 1, wherein said protein transduction domain has at least 60% sequence identity to the amino acid sequence of the TAT protein transduction domain (SEQ ID NO:54), said domain having TAT transduction activity.

4. The method of claim 3, wherein said protein transduction domain has at least 70% sequence identity to the amino acid sequence of the TAT protein transduction domain (SEQ ID NO: 54).

5. The method of claim 1, wherein said pharmaceutical composition is administered at least every other day or once a day.

* * * * *

UNITED STATES PATENT AND TRADEMARK OFFICE
CERTIFICATE OF CORRECTION

PATENT NO.        : 8,226,930 B2
APPLICATION NO.   : 12/295856
DATED             : July 24, 2012
INVENTOR(S)       : Franco Antonio Laccone It is certified that error appears in the above-identified patent and that said Letters Patent is hereby corrected as shown below:

On the Title Page of the patent:

The line providing the Assignee information should read
-- (73) Assignee: Georg-August-Universitat Gottingen Stiftung Offentlichen Rechts, Gottingen (DE) --

Signed and Sealed this
Eighth Day of January, 2013

David J. Kappos
*Director of the United States Patent and Trademark Office*